United States Patent
Rajadas

(10) Patent No.: US 11,400,049 B2
(45) Date of Patent: Aug. 2, 2022

(54) PEGYLATED LIPOSOMAL FORMULATIONS OF APELIN FOR TREATMENT OF CARDIOVASCULAR-RELATED DISEASES

(71) Applicant: Avive, Inc., Sunnyvale, CA (US)

(72) Inventor: Jayakumar Rajadas, Cupertino, CA (US)

(73) Assignee: Avive, Inc., Sunnyvale, CA (US)

( * ) Notice: Subject to any disclaimer, the term of this patent is extended or adjusted under 35 U.S.C. 154(b) by 0 days.

(21) Appl. No.: 16/342,506

(22) PCT Filed: Oct. 19, 2017

(86) PCT No.: PCT/US2017/057476
§ 371 (c)(1),
(2) Date: Apr. 16, 2019

(87) PCT Pub. No.: WO2018/075822
PCT Pub. Date: Apr. 26, 2018

(65) Prior Publication Data
US 2020/0054556 A1 Feb. 20, 2020

Related U.S. Application Data

(60) Provisional application No. 62/410,160, filed on Oct. 19, 2016, provisional application No. 62/464,594, filed on Feb. 28, 2017.

(51) Int. Cl.
A61K 9/127 (2006.01)
A61P 15/10 (2006.01)
(Continued)

(52) U.S. Cl.
CPC .......... *A61K 9/1271* (2013.01); *A61K 9/1277* (2013.01); *A61K 38/1709* (2013.01);
(Continued)

(58) Field of Classification Search
CPC ................ A61K 9/1271; A61K 9/1277; A61K 38/1709; A61K 45/06; A61K 9/19;
(Continued)

(56) References Cited

U.S. PATENT DOCUMENTS

| 4,338,397 A | 7/1982 | Gilbert et al. |
|---|---|---|
| 4,425,437 A | 1/1984 | Riggs |

(Continued)

FOREIGN PATENT DOCUMENTS

| CN | 10195379 A | 1/2011 |
|---|---|---|
| JP | 2014506922 A | 3/2014 |

(Continued)

OTHER PUBLICATIONS

Kawahara, H., et al in PLOS One, vol. 8, issue 6, pp. 1-7, Jun. 2013.*

(Continued)

*Primary Examiner* — Gollamudi S Kishore
(74) *Attorney, Agent, or Firm* — Morrison & Foerster LLP

(57) ABSTRACT

The disclosure relates generally to compositions comprising pegylated liposomal formulations of apelin for the treatment of cardiovascular-related diseases.

22 Claims, 14 Drawing Sheets

Specification includes a Sequence Listing.

A

B

(51) Int. Cl.
| | |
|---|---|
| *A61P 9/10* | (2006.01) |
| *A61P 3/10* | (2006.01) |
| *A61P 9/12* | (2006.01) |
| *A61P 13/12* | (2006.01) |
| *A61P 9/04* | (2006.01) |
| *A61K 38/17* | (2006.01) |
| *A61K 45/06* | (2006.01) |

(52) U.S. Cl.
CPC ............... *A61K 45/06* (2013.01); *A61P 3/10* (2018.01); *A61P 9/04* (2018.01); *A61P 9/10* (2018.01); *A61P 9/12* (2018.01); *A61P 13/12* (2018.01); *A61P 15/10* (2018.01)

(58) Field of Classification Search
CPC ........ A61K 47/24; A61K 47/10; A61K 47/28; A61P 15/10; A61P 9/10; A61P 3/10; A61P 9/12; A61P 13/12; A61P 9/04; A61P 9/00; A61P 11/00
See application file for complete search history.

(56) References Cited

U.S. PATENT DOCUMENTS

| | | | |
|---|---|---|---|
| 4,431,739 A | 2/1984 | Riggs | |
| 4,631,211 A | 12/1986 | Houghten | |
| 4,873,192 A | 10/1989 | Kunkel | |
| 5,831,005 A | 11/1998 | Zuckerman et al. | |
| 5,877,278 A | 3/1999 | Zuckerman et al. | |
| 5,977,301 A | 11/1999 | Zuckerman et al. | |
| 7,947,280 B2 | 5/2011 | Ashley et al. | |
| 8,946,382 B2 | 2/2015 | Cuttitta et al. | |
| 2005/0112065 A1* | 5/2005 | Drummond | A61K 47/18 424/9.321 |
| 2008/0182779 A1* | 7/2008 | Ashley | A61P 9/04 424/133.1 |
| 2009/0092663 A1* | 4/2009 | Ponzoni | A61K 31/704 424/450 |
| 2011/0104261 A1* | 5/2011 | Drummond | A61K 9/1272 424/450 |
| 2013/0164370 A1 | 6/2013 | Pumeranz et al. | |
| 2013/0183236 A1 | 7/2013 | Rogers et al. | |
| 2014/0134232 A1* | 5/2014 | Boulikas | C12N 15/88 424/450 |
| 2014/0142022 A1 | 5/2014 | Zecri et al. | |
| 2014/0142049 A1 | 5/2014 | Jia et al. | |
| 2015/0010616 A1* | 1/2015 | Yuk | A61K 9/5146 424/450 |
| 2015/0064115 A1* | 3/2015 | Ashizawa | A61K 47/6915 424/9.321 |
| 2016/0058705 A1 | 3/2016 | Rajadas et al. | |
| 2016/0074324 A1* | 3/2016 | Yang | A61K 47/14 424/450 |
| 2016/0193168 A1 | 7/2016 | Nicolls et al. | |

FOREIGN PATENT DOCUMENTS

| | | |
|---|---|---|
| WO | 2012102363 A1 | 8/2012 |
| WO | 2012118376 A1 | 9/2012 |
| WO | WO-2013/111110 A2 | 8/2013 |
| WO | WO-2015/013169 A2 | 1/2015 |
| WO | WO-2015/188073 A1 | 12/2015 |
| WO | WO-2018/075822 A1 | 4/2018 |

OTHER PUBLICATIONS

Ahn, D. et al. (Mar. 1, 2004). "Induction of Myocardial Infarcts of a Predictable Size and Location by Branch Pattern Probability-Assisted Coronary Ligation in C57BL/6 Mice," *Am J Physiol Heart Circ Physiol* 286(3):H1201-H1207.

Andersen, C.U. et al. (Jul.-Sep. 2011). "Apelin and Pulmonary Hypertension", Pulm. Circ. 1:334-346.

Ashley, E.A. et al. (Jan. 1, 2005). "The Endogenous Peptide Apelin Potently Improves Cardiac Contractility and Reduces Cardiac Loading In Vivo", Cardiovasc. Res. 65(1):73-82, 16 pages.

Azizi, Y. et al. (2013, e-pub. May 29, 2013). "Post-Infarct Treatment with [Pyr1]-Apelin-13 Reduces Myocardial Damage Through Reduction of Oxidative Injury and Nitric Oxide Enhancement in the Rat Model of Myocardial Infarction", Peptides 46:76-82.

Cayabyab, M. et al. (Dec. 2000). "Apelin, the Natural Ligand of the Orphan Seven-Transmembrane Receptor APJ, Inhibits Human Immunodeficiency Virus Type 1 Entry", J. Virol. 74(24):11972-11976.

Chakrabarti, S. et al. (2016, e-pub. Dec. 29, 2015). "Bioactive Peptides on Endothelial Function," *Food Sci Human Wellness* 5(1):1-7.

Charles, C.J. (Jun. 2011, e-pub. Mar. 24, 2011). "Update on Apelin Peptides as Putative Targets for Cardiovascular Drug Discovery", Expert Opin. Drug Discov. 6(6):633-644.

Choi, K.Y. et al. (Nov. 22, 2011, e-pub. Oct. 11, 2011). "Smart Nanocarrier Based on Pegylated Hyaluronic Acid for Cancer Therapy", ACS Nano 5(11):8591-8599.

Chono, S. et al. (Jul. 20, 2009, e-pub. Apr. 5, 2009). "Aerosolized Liposomes with Dipalmitoyl Phosphatidylcholine Enhance Pulmonary Insulin Delivery", J. Control Release Off. J. Control Release Soc. 137(2):104-109.

Cray, C. et al. (Dec. 2009). "Acute Phase Response in Animals: A Review", Comp Med 59(6):517-526.

Dalbie-Mcfarland, G. et al. (Nov. 1982). "Oligonucleotide-Directed Mutagenesis as a General and Powerful Method for Studies of Protein Function", Proc. Natl. Acad. Sci USA 79(21):6409-6413.

Dayhoff, M.O. et al. (1978). "A Model of Evolutionary Change in Proteins", Chapter 22 in Atlas of Protein Sequence and Structure, Washington DC: Nat. Biomed. Res. 5(3):353-358.

De Jong, W.H. et al. (Jun. 2008). "Drug Delivery and Nanoparticles: Applications and Hazards", Int. J. Nanomedicine 3(2):133-149.

DeAlmeida, A.C. et al. (2010, e-pub. Apr. 21, 2010). "Transverse Aortic Constriction in Mice", J. Vis. Exp. (38):1729, 3 pages.

Edge, M.D. et al. (Aug. 20, 1981). "Total Synthesis of a Human Leukocyte Interferon Gene", Nature 292(5825):756-762.

El Messari, S. et al. (Sep. 2004). "Functional Dissociation of Apelin Receptor Signaling And Endocytosis: Implications For The Effects of Apelin on Arterial Blood Pressure", J. Neurochem. 90(6):1290-1301.

Erdmann, K. et al. (2008). "The Possible Roles of Food-Derived Bioactive Peptides in Reducing the Risk of Cardiovascular Disease," *J Nutr Biochem* 19(10):643-654.

Fan, X et al. (Sep. 2, 2003). "Structural and Functional Study of the Apelin-13 Peptide, an Endogenous Ligand of the HIV-1 Coreceptor, APJ", Biochemistry 42(34):10163-10168.

Fenske, D.B. et al. (Jun. 6, 2001). "Cationic Poly(ethyleneglycol) Lipids Incorporated into Pre-Formed Vesicles Enhance Binding and Uptake to BHK Cells", Biochim. Biophys. Acta 1512(2):259-272.

Frey, N. et al. (2003, e-pub. Jan. 9, 2003). "Cardiac Hypertrophy: The Good, The Bad, and The Ugly", Annu. Rev. Physiol. 65:45-79.

Frey, N. et al. (Apr. 6, 2004). "Hypertrophy of the heart: a new therapeutic target?", Circulation 109(13):1580-1589.

Gruys, E. et al. (Nov. 2005, e-pub. Oct. 28, 2005). "Acute Phase Reaction and Acute Phase Proteins", J. Zhejiang Univ. Sci. B 6(11):1045-1056.

Gunaseelan, S. et al. (Mar. 18, 2010, e-pub. Nov. 24, 2009). "Surface Modifications of Nanocarriers for Effective Intracellular Delivery of Anti-HIV Drugs", Adv. Drug Deliv. Rev. 62(4-5):518-531, 38 pages.

Hackland, A.F. et al. (1994). "Coat Protein-Mediated Resistance in Transgenic Plants", Arch. Virol. 139(1-2):1-22.

Hajipour, M.J. et al. (2014). "Personalized Protein Coronas: A "key" Factor at the Nanobiointerface", Biomater Sci 2(9):1210-1221.

Harris J.M. et al. (Mar. 2003). "Effect of Pegylation on Pharmaceuticals", Nat Rev Drug Discov 2(3):214-221.

Houghten, R.A. (Aug. 1985). "General Method for the Rapid Solid-Phase Synthesis of Large Numbers of Peptides: Specificity of Antigen-Antibody Interaction at the Level of Individual Amino Acids", Proc. Natl. Acad. Sci. USA 82(15):5131-5135.

(56) References Cited

OTHER PUBLICATIONS

Iemitsu, M. et al. (Dec. 2001). "Physiological and Pathological Cardiac Hypertrophy Induce Different Molecular Phenotypes in the Rat", Am. J. Physiol. Regul. Integr. Comp. Physiol. 281(6):R2029-2036.

Immordino, M.L. et al. (Sep. 2006). "Stealth Liposomes: Review of the Basic Science, Rationale, and Clinical Applications, Existing and Potential", Int. J. Nanomedicine, 1(3):297-315.

International Preliminary Report on Patentability dated May 2, 2019, for PCT Patent Application No. PCT/US2017/057476, filed Oct. 19, 2017, 8 pages.

International Search Report and Written Opinion of the International Searching Authority dated Jan. 12, 2018, for PCT Patent Application No. PCT/US2017/057476, filed Oct. 19, 2017, 11 pages.

Japp, A.G. et al. (Apr. 27, 2010, e-pub. Apr. 12, 2010). "Acute Cardiovascular Effects of Apelin in Humans: Potential Role in Patients with Chronic Heart Failure", Circulation 121(16):1818-1827.

Japp, A.G. et al. (Sep. 9, 2008). "Vascular Effects of Apelin In Vivo In Man", J. Am. Coll. Cardiol. 52(11):908-913.

Jay, E. et al. (May 25, 1984). "Chemical Synthesis of a Biologically Active Gene for Human Immune Interferon-Gamma. Prospect for Site-Specific Mutagenesis and Structure-Function Studies", J. Biol. Chem. 259(10):6311-6317.

Jia, Z.Q. et al. (Nov. 2012, e-pub. Sep. 7, 2012). "Cardiovascular Effects of a PEGylated Apelin", Peptides 38(1):181-188.

Jones, L.K. et al. (Oct. 2009, e-pub. E-pub. May 22, 2009). "IL-1RI Deficiency Ameliorates Early Experimental Renal Interstitial Fibrosis," Nephrol Dial Transplant 24(10):3024-3032.

Katugampola, S.D. et al. (Mar. 2001). "[125I]-(Pyr1)Apelin-13 is a Novel Radioligand for Localizing the APJ Orphan Receptor in Human and Rat Tissues with Evidence for a Vasoconstrictor Role in Man", Br. J. Pharmacol. 132(6):1255-1260.

Kibria, G. et al. (Jul. 30, 2011, e-pub. Apr. 5, 2011). "Dual-Ligand Modification of PEGylated Liposomes Shows Better Cell Selectivity and Efficient Gene Delivery", J. Control Release Off J. Control Release Soc. 153(2):141-148.

Kim, A. et al. (Mar. 25, 1999). "Pharmacodynamics of Insulin in Polyethylene Glycol-Coated Liposomes", Int. J. Pharm. 180(1):75-81.

Kleinz, M.J. et al. (Feb. 7, 2008, e-pub. Oct. 22, 2007). "Apelin reduces myocardial reperfusion injury independently of PI3K/Akt and P70S6 kinase", Regul. Pept. 146:271-277.

Koguchi, W. et al. (2012, e-pub. Nov. 12, 2011). "Cardioprotective Effect of Apelin-13 on Cardiac Performance and Remodeling in End-Stage Heart Failure", Circ. J. Off. J. Jpn. Circ. Soc. 76(1):137-144.

Koren, M.J. et al. (Mar. 1, 1991). "Relation of Left Ventricular Mass and Geometry to Morbidity and Mortality in Uncomplicated Essential Hypertension", Ann. Intern. Med. 114(5):345-352.

Kuba, K. et al. (Aug. 17, 2007, e-pub. Aug. 2, 2007). "Impaired Heart Contractility in Apelin Gene-Deficient Mice Associated with Aging and Pressure Overload", Circ. Res. 101(4):e32-42.

Kumar, A. et al. (Sep.-Oct. 2013, e-pub. Oct. 27, 2012). "Gold Nanoparticles: Emerging Paradigm for Targeted Drug Delivery System", Biotechnol Adv. 31(5):593-606.

Kunkel, T.A. (Jan. 1985). "Rapid and Efficient Site-Specific Mutagenesis without Phenotypic Selection", Proc. Natl. Acad. Sci. USA 82(2):488-492.

Kunkel, T.A. et al. (1987). "Rapid and Efficient Site-Specific Mutagenesis Without Phenotypic Selection", Methods Enzymol. 154:367-382.

Langelaan, D.N. et al. (Jan. 27, 2009). "Structural Insight into G-Protein Coupled Receptor Binding by Apelin", Biochemistry 48(3):537-548.

Langelaan, D.N. et al. (Jun. 2013, Feb. 22, 2013). "Structural Features of the Apelin Receptor N-Terminal Tail and First Transmembrane Segment Implicated in Ligand Binding and Receptor Trafficking", Biochim. Biophys. Acta 1828(6):1471-1483.

Lee, D.K. et al. (Jan. 2000). "Characterization of Apelin, the Ligand for the APJ Receptor", J. Neurochem. 74(1):34-41.

Lee, H. et al. (May 2003). "N-Terminal Site-Specific Mono-PEGylation of Epidermal Growth Factor", Pharm. Res. 20(5):818-825.

Leeper, N.J. et al. (May 2009, e-pub. Mar. 20, 2009). "Apelin Prevents Aortic Aneurysm Formation by Inhibiting Macrophage Inflammation", Am. J. Physiol. Heart Circ. Physiol. 296:H1329-1335.

Levy, D. et al. (May 31, 1990). "Prognostic Implications of Echocardiographically Determined Left Ventricular Mass in the Framingham Heart Study", N. Engl. J. Med. 322(22):1561-1566.

Li, C.L. et al. (2010, e-pub. Mar. 7, 2010). "Development of Pegylated Liposomal Vinorelbine Formulation Using 'Post-Insertion' Technology", International Journal of Pharmaceutics 391:230-236.

Liao, Y. et al. (May 2002). "Echocardiographic Assessment of LV Hypertrophy and Function in Aortic-Banded Mice: Necropsy Validation", Am. J. Physiol. Heart Circ. Physiol. 282(5):H1703-1708.

Maguire, J.J. et al. (Sep. 2009, e-pub. Jul. 13, 2009). "[Pyr1]apelin-13 Identified as the Predominant Apelin Isoform in the Human Heart: Vasoactive Mechanisms and Inotropic Action in Disease", Hypertension 54(3):598-604.

Mahmoudi, M. et al. (Jan.-Feb. 2011, May 26, 2010). "Superparamagnetic Iron Oxide Nanoparticles (SPIONs): Development, Surface Modification and Applications in Chemotherapy", Adv. Drug Deliv. Rev. 63(1-2):24-46.

Mahmoudi, M. et al. (Sep. 14, 2011, e-pub. Jun. 21, 2011). "Protein-Nanoparticle Interactions: Opportunities and Challenges", Chem. Rev. 111(9):5610-5637.

Mahon, E. et al. (Jul. 20, 2012, e-pub. Apr. 10, 2012). "Designing the nanoparticle-biomolecule interface for Targeting and Therapeutic Delivery", J. Control Release 161(2):164-174.

Mesmin, C. et al. (Dec. 2012). "MS-based Approaches to Unravel the Molecular Complexity of Proprotein-Derived Biomarkers and Support Their Quantification: The Examples Of B-Type Natriuretic Peptide and Apelin Peptides", Bioanalysis 4(23):2851-2863.

Monopoli, M.P. et al. (Dec. 2012). "Biomolecular Coronas Provide the Biological Identity of Nanosized Materials", Nat. Nanotechnol. 7(12):779-786.

Monopoli, M.P. et al. (Mar. 2, 2011). "Physical-Chemical Aspects of Protein Corona: Relevance to in Vitro and in Vivo Biological Impacts of Nanoparticles", J. Am. Chem. Soc. 133(8):2525-2534.

Murza et al. (2014, e-pub. Apr. 11, 2014). "Stability and Degradation Patterns of Chemically Modified Analogs of Apelin-13 in Plasma and Cerebrospinal Fluid", Bio Polymers 101(4):297-303.

Murza, A. et al. (Feb. 6, 2012). "Elucidation of the Structure-Activity Relationships of Apelin: Influence of Unnatural Amino Acids on Binding, Signaling, and Plasma Stability", ChemMedChem. 7(2):318-325.

Nag, O.K. et al. (Dec. 2013, e-pub. Oct. 25, 2013). "Surface Engineering of Liposomes for Stealth Behavior", Pharmaceutics 5(4):542-569.

Nakamura, A. et al. (Sep. 2001). "LV Systolic Performance Improves with Development of Hypertrophy After Transverse Aortic Constriction in Mice", Am. J. Physiol. Heart Circ. Physiol. 281(3):H1104-1112.

Nambair, K.P. et al. (Mar. 23, 1984). "Total Synthesis and Cloning of a Gene Coding for the Ribonuclease S Protein", Science 223(4642):1299-1301.

Nguyen, J.T. et al. (Jul. 2000, Jun. 12, 2000). "Improving SH3 Domain Ligand Selectivity Using a Non-Natural Scaffold", Chem Biol. 7(7):463-473.

Olson, E.N. (May 2004). "A Decade of Discoveries in Cardiac Biology", Nat. Med. 10(5):467-474.

Parasuraman, S. et al. (Jul.-Dec. 2010). "Blood Sample Collection in Small Laboratory Animals", J. Pharmacol. Pharmacother. 1(2):87-93.

Patten, R. D. et al. (May 1998). "Ventricular Remodeling in a Mouse Model of Myocardial Infarction," Am J. Physiol 274(5):H1812-H1820. (Also Cited as: Am. J. Physiol. 274 (Heart Circ. Physiol. 43): H1812-H1820).

(56) References Cited

OTHER PUBLICATIONS

Patten, R.D. et al. (Mar. 2009). "Small Animal Models of Heart Failure: Development of Novel Therapies, Past and Present", Circ. Heart Fail. 2(2):138-144.
Pisarenko, O.I. et al. (Jul.-Sep. 2013). "Effects of Structural Analogues of Apelin-12 in Acute Myocardial Infarction in Rats", J. Pharmacol. Pharmacother. 4(3):198-203.
Pisarenko, O.I. et al. (Jun. 2014, e-pub. Mar. 6, 2014). "Apelin-12 and its Structural Analog Enhance Antioxidant Defense in Experimental Myocardial Ischemia and Reperfusion", Mol. Cell. Biochem. 391(1-2):241-250.
Pitkin, S.L. et al. (Aug. 2010). "Modulation of the Apelin/APJ System in Heart Failure and Atherosclerosis in Man", Br. J. Pharmacol. 160(7):1785-1795.
Porta, C. et al. (Jun. 1996). "Use of Viral Replicons for the Expression of Genes in Plants", Mol. Biotech. 5(3):209-221.
Rezler, E.M. et al. (2007). "Peptide-Mediated Targeting of Liposomes to Tumor Cells", Methods Mol. Biol. 386:269-298.
Rezler, E.M. et al. (Apr. 25, 2007, e-pub. Mar. 31, 2007). "Targeted Drug Delivery Utilizing Protein-Like Molecular Architecture", J. Am. Chem. Soc. 129(16):4961-4972, 26 pages.
Roberts, M.J. et al. (Jun. 17, 2002). "Chemistry for Peptide and Protein PEGylation", Adv. Drug Deliv. Rev. 54(4):459-476.
Robinson, S.N. et al. (Nov.-Dec. 2002). "Sustained Release of Growth Factors", In Vivo 16(6):535-540.
Rockman, H. A. et al. (Sep. 15, 1991). "Segregation of Atrial-Specific and Inducible Expression of an Atrial Natriuretic Factor Transgene in an in Vivo Murine Model of Cardiac Hypertrophy", Proc. Natl. Acad. Sci. U.S.A. 88(18):8277-8281.
Rosenson, R.S. et al. (Sep. 1993). "Myocardial Injury: The Acute Phase Response and Lipoprotein Metabolism", J. Am. Coll. Cardiol. 22(3):933-940.
Sanchez, O. et al. (Jan. 7, 2002). "Acute Stress-Induced Tissue Injury in Mice: Differences Between Emotional and Social Stress", Cell Stress Chaperones 7(1):36-46.
Scimia, M.C. et al. (Aug. 16, 2012). "APJ Acts as a Dual Receptor in Cardiac Hypertrophy", Nature 488(7411):394-398, 12 pages.
Selby, M.J. et al. (Jun. 1993). "Expression, Identification and Subcellular Localization of the Proteins Encoded by the Hepatitis C Viral Genome", J. Gen. Virol. 74(Pt 6):1103-1113.
Serpooshan, V. et al. (Jan. 30, 2015). "[Pyr1]-Apelin-13 Delivery Via Nano-Liposomal Encapsulation Attenuates Pressure Overload-Induced Cardiac Dysfunction," Biomaterials 37:289-298, 22 pages.
Simon, R.J. et al. (Oct. 15, 1992). "Peptoids: A Modular Approach to Drug Discovery", Proc. Natl. Acad. Sci. USA 89(20):9367-9371.
Simpkin, J.C. et al. (Nov. 2007, e-pub. Aug. 13, 2007). "Apelin-13 and Apelin-36 Exhibit Direct Cardioprotective Activity Against Ischemiareperfusion Injury", Basic Res. Cardiol. 102(6):518-528.
Smith, T.F. et al. (Dec. 1981). "Comparison of Biosequences", Advances in Appl. Math. 2(4):482-489.
Stemmer, W.P. et al. (Oct. 16, 1995). "Single-Step Assembly of a Gene and Entire Plasmid from Large Numbers of Oligodeoxyribonucleotides", Gene 164(1):49-53.
Supavekin, S. et al. (May 2003). "Differential Gene Expression Following Early Renal Ischemia/Reperfusion," Kidney Int. 63(5):1714-1724.
Szokodi, I. et al. (Sep. 6, 2002). "Apelin, the Novel Endogenous Ligand of the Orphan Receptor APJ, Regulates Cardiac Contractility", Circ. Res. 91(5):434-440.
Tamargo, J. et al. (Nov. 2011). "New Therapeutic Targets for the Development of Positive Inotropic Agents", Discov. Med. 12(66):381-392.
Tasci, I. et al. (Jul. 2007). "Plasma Apelin is Lower in Patients with Elevated LDL-Cholesterol", Exp. Clin. Endocrinol. Diabetes 115(7):428-432.
Tatemoto, K. et al. (Oct. 20, 1998). "Isolation and Characterization Of A Novel Endogenous Peptide Ligand For The Human APJ Receptor", Biochem. Biophys. Res. Commun. 251(2):471-476.
Tomei, L. et al. (Jul. 1993). "NS3 is a Serine Protease Required for Processing of Hepatitis C Virus Polyprotein", J. Virol. 67(7):4017-4026.
Van Nierop, B.J. et al. (2013, e-pub. Feb. 1, 2013). "Phenotyping of Left and Right Ventricular Function in Mouse Models of Compensated Hypertrophy and Heart Failure with Cardiac MRI", PLoS One 8(2):e55424, 9 pages.
Vestbo, J. et al. (May 2013, e-pub. Sep. 27, 2012). "The Study to Understand Mortality and Morbidity in COPD (SUMMIT) Study Protocol," Eur Respir J 41(5):1017-1022.
Vestbo, J. et al. (Sep. 2015). "Study To Understand Mortality and Morbidity In COPD (SUMMIT)," Eur Respir J 46(Suppl. 59):OA3476 (2 pages).
Visser, C.C. et al. (Jun. 2005, e-pub. Apr. 18, 2005). "Targeting Liposomes with Protein Drugs to the Blood-Brain Barrier In Vitro", Eur. J. Pharm. Sci. 25(2-3):299-305.
Wang, W. et al. (Aug. 2013, e-pub. Aug. 23, 2013). "Loss of Apelin Exacerbates Myocardial Infarction Adverse Remodeling and Ischemia-reperfusion Injury: Therapeutic Potential of Synthetic Apelin Analogues", J. Am. Heart Assoc. 2(4):e000249, 17 pages.
Woodle, M.C. et al. (Apr. 13, 1992). "Versatility in Lipid Compositions Showing Prolonged Circulation with Sterically Stabilized Liposomes", Biochim Biophys Acta 1105(2):193-200.
Xie, Y. et al. (Jun. 20, 2005). "Transport Of Nerve Growth Factor Encapsulated Into Liposomes Across The Blood-Brain Barrier: In Vitro And In Vivo Studies", J. Control Release Off. J. Control. Release Soc. 105(1-2):106-119.
Zhang, B.H. et al. (Sep. 2014, e-pub. Oct. 19, 2013). "Cardioprotective Effects of Adipokine Apelin on Myocardial Infarction", Heart Vessels 29(5):679-689.
Zhang, H. (2012). "Design and Synthesis of Antithrombotic Liposomal Protein Conjugate", ETD Archive, paper, 319, 192 pages, located at: https://engagedscholarship.csuohio.edu/cgi/viewcontent.cgi?referer=https://scholar.google.com/&httpsredir=1&article=1318&context=etdarchive, last visited Sep. 10, 2019.
Zhang, Y. et al. (Jun. 1, 2014, e-pub. Apr. 13, 2014). "Identifying Structural Determinants of Potency for Analogs of Apelin-13: Integration Of C-Terminal Truncation With Structure-Activity", Bioorg. Med. Chem. 22(11):2992-2997.
Zhou, N. et al. (Dec. 5, 2003). "The N-Terminal Domain Of APJ, A CNS-Based Coreceptor for HIV-1, Is Essential For Its Receptor Function And Coreceptor Activity", Virology 317(1):84-94.
Zoller, M.J. (1983). "Oligonucleotide-Directed Mutagenesis of DNA Fragments Cloned into M13 Vectors", Methods Enzymol. 100:468-500.
Herce, H.D. et al. (Oct. 2019). "Arginine-Rich Peptides Destabilize the Plasma Membrane, Consistent with a Pore Formation Translocation Mechanism of Cell-Penetrating Peptides", Biophysical Journal 97(7):1917-1925.
Jin, H.R. et al. (Dec. 2009, e-pub. Sep. 1, 2009). "Functional and Morphologic Characterizations of the Diabetic Mouse Corpus Cavernosum: Comparison of a Multiple Low-Dose and a Single High-Dose *Streptozotocin* Protocols," J Sex Med 6(12):3289-3304.
Ryu, J.K. et al. (Jul. 2009, e-pub. Apr. 23, 2009). "Derangements in Endothelial Cell-To-Cell Junctions Involved In The Pathogenesis Of Hypercholesterolemia-Induced Erectile Dysfunction," J Sex Med 6(7):1893-1907.

\* cited by examiner

*: Significantly different ( p<0.05 ) compared with Sham group;
^: Significantly different ( p<0.05 ) compared with Control group;

A

B

A

B

A

B

A

B

A

* Significantly different (p<0.05) compared with Sham group;
^ Significantly different (p<0.05) compared with Control group;

Endothelial functions of bioactive peptides.

| Endothelial functions | Peptide |
|---|---|
| Antioxidant | Glutathione |
| Antioxidant, ACE-inhibitor, anti-inflammatory | Ile-Arg-Trp |
| Antioxidant, ACE-inhibitor, anti-inflammatory | Ile-Gln-Trp |
| NO generation | NOP-47 |
| NO generation/opioid agonist | Aα-lactorphin (Tyr-Gly-Leu-Phe) |
| NO generation/opioid agonist | Aβ-lactorphin (Tyr-Leu-Leu-Phe) |
| NO generation | Arg-Ala-Asp-His-Pro-Phe |
| NO generation | Arginine-rich cationic peptides |
| NO generation | Carnosine |
| NO generation | Casomokinin L (Tyr-Pro-Phe-Pro-Pro-Leu) |
| Anti-inflammatory | Leu-Asp-Ala-Val-Asn-Arg |
| Anti-inflammatory | Met-Met-Leu-Asp-Phe |
| ACE inhibition | Val-Tyr |
| ACE inhibition | Val-Pro-Pro |
| ACE inhibition, ACE2 upregulation | Ile-Pro-Pro |
| ACE inhibition | Peptide-rich hydrolysate |
| AT1R blocker | Leu-Ile-Trp-Lys-Leu |
| AT1R blocker | Arg-Pro-Tyr-Leu |
| Renin downregulation, AT1R blocker | Arg-Val-Pro-Ser-Leu |

Examples of ACE inhibitory peptides with in vivo antihypertensive effects

| Origin | Sequence/name |
|---|---|
| Milk (β-casein) | VPP |
| | IPP |
| Milk (β-lactoglobulin) | IPA (β-lactosin A) |
| | ALPM (β-lactosin B) |
| Fish (sardine muscle) | VY |
| Fish (bonito muscle) | LKPNM |
| | LKP |
| Meat (chicken muscle) | LKP |
| | IKW |
| | LAP |
| Meat (porcine muscle) | MNPRK (myopentapeptide A) |
| | ITTNP (myopentapeptide B) |
| Egg (ovalbumin) | LW |
| Soy (glycinin) | NWGPLV |
| Wheat (gliadin) | IAP |

Examples of bioactive peptides derived from food

| Activity | Origin | Sequence/name |
|---|---|---|
| Antioxidant | Fish (sardine muscle) | MY |
| | Soy (β-conglycinin) | LLPHH |
| | Milk (casein) | YFYPEL |
| | Milk (β-lactoglobulin) | MHIRL, YVEEL, WYSLAMAASDI |
| | Egg (egg white) | YAEERYPIL |
| Antihrombotic | Milk (κ-casein) | MAIPPKKNQDK (casoplatelin) and smaller fragments |
| | Milk (lactoferrin) | KRDS |
| Hypocholesterolemic | Soy (glycinin) | LPYPR |
| | Soy (glycinin) | IAVPGEVA |
| | Soy (β-conglycinin) | Several peptide fragments (e.g., sequence corresponding to the residues 127-150) |
| | Milk ((β-lactoglobulin) | IIAEK (lactostatin) |
| Hypotriglyceridemic | Blood (globin) | VVYP, VYP, VTL |
| Antiobese | Soy (β-conglycinin) | VRIRLLQRFNKRS |
| | Milk (κ-casein) | Caseinoglycomacropeptide |

Examples of commercially available functional foods carrying bioactive peptides (modified from Hartmann and Meisel [1])

| Brand name | Manufacturer | Remarks | Bioactive peptides | Health claim |
|---|---|---|---|---|
| Calpis | Calpis Co., Japan | Sour milk | VPP; IPP | Hypotensive |
| Evolus | Valio, Finland | Fermented milk | VPP; IPP | Hypotensive |
| Casein DP | Kanebo Ltd., Japan | Casein hydrolysate | FFVAPFPEVFGK | Hypotensive |
| C12 peptide | DMV International, Netherlands | Casein hydrolysate | FFVAPFPEVFGK | Hypotensive |
| BioZate | Davisco, USA | Whey protein hydrolysate | Whey-derived peptides | Hypotensive |
| Peptide Soup | NIPPON, Japan | Soup | Bonito-derived peptides | Hypotensive |
| BioPURE-GMP | Davisco, USA | Whey protein hydrolysate | Glycomacropeptide | Antithrombotic, antimicrobial, anticariogenic |
| CholesteBlock | Kyowa Hakko, Japan | Soft drink | Soy-derived peptides bound to phospholipids | Hypocholesterolemic |

SEQUENCE LISTING

<160> NUMBER OF SEQ ID NOS: 7

<210> SEQ ID NO 1
<211> LENGTH: 77
<212> TYPE: PRT
<213> ORGANISM: Homo sapiens
<300> PUBLICATION INFORMATION:
<308> DATABASE ACCESSION NUMBER: NP_059109.3
<309> DATABASE ENTRY DATE: 2017-10-03
<313> RELEVANT RESIDUES IN SEQ ID NO: (1)..(77)

<400> SEQUENCE: 1

Met Asn Leu Arg Leu Cys Val Gln Ala Leu Leu Leu Trp Leu Ser
1               5                   10                  15

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
        35                  40                  45

Arg Asn Gly Pro Gly Pro Trp Gln Gly Arg Arg Lys Phe Arg Arg
    50                  55                  60

Gln Arg Pro Arg Leu Ser His Lys Gly Pro Met Pro Phe
65                  70                  75

<210> SEQ ID NO 2
<211> LENGTH: 12
<212> TYPE: PRT
<213> ORGANISM: Homo sapiens

<400> SEQUENCE: 2

Arg Pro Arg Leu Ser His Lys Gly Pro Met Pro Phe
1               5                   10

<210> SEQ ID NO 3
<211> LENGTH: 13
<212> TYPE: PRT
<213> ORGANISM: Homo sapiens

<400> SEQUENCE: 3

Gln Arg Pro Arg Leu Ser His Lys Gly Pro Met Pro Phe
1               5                   10

<210> SEQ ID NO 4
<211> LENGTH: 13
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is any amino acid

<400> SEQUENCE: 4

Xaa Arg Pro Arg Leu Ser His Lys Gly Pro Met Pro Phe
1               5                   10

<210> SEQ ID NO 5
<211> LENGTH: 17
<212> TYPE: PRT
<213> ORGANISM: Homo sapiens

<400> SEQUENCE: 5

```
Lys Phe Arg Arg Gln Arg Pro Arg Leu Ser His Lys Gly Pro Met Pro
1               5                   10                  15

Phe

<210> SEQ ID NO 6
<211> LENGTH: 19
<212> TYPE: PRT
<213> ORGANISM: Homo sapiens

<400> SEQUENCE: 6

Arg Arg Lys Phe Arg Arg Gln Arg Pro Arg Leu Ser His Lys Gly Pro
1               5                   10                  15

Met Pro Phe

<210> SEQ ID NO 7
<211> LENGTH: 36
<212> TYPE: PRT
<213> ORGANISM: Homo sapiens

<400> SEQUENCE: 7

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
                20                  25                  30

Pro Met Pro Phe
            35
```

PEGYLATED LIPOSOMAL FORMULATIONS OF APELIN FOR TREATMENT OF CARDIOVASCULAR-RELATED DISEASES

CROSS-REFERENCE TO RELATED APPLICATIONS

This application is a national stage application under 35 U.S.C. § 371 of International Application No. PCT/US2017/057476, filed on Oct. 19, 2017, which claims priority to U.S. Provisional Application No. 62/410,160, filed on Oct. 19, 2016, and U.S. Provisional Application No. 62/464,594, filed on Feb. 28, 2017, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 185632000300SEQLIST.TXT, date recorded: Apr. 16, 2019, size: 3 KB).

FIELD

The present disclosure provides compositions of apelin, for example, pegylated liposomal formulations of apelin, and methods for treating cardiovascular-related diseases and disorders.

BACKGROUND

Apelin is the endogenous ligand for the G-protein-coupled APJ receptor that regulates a variety of biological functions including body fluid homeostasis, blood pressure, heart development and function, and multi-vascular remodeling. The therapeutic use of apelin peptides have been limited by its significantly short plasma half-life from rapid metabolism of the bioactive peptide in vivo.

As such, there remains a need for apelin formulations having enhanced stability and therapeutic efficacy.

SUMMARY

In some aspects provided herein are compositions comprising an effective amount of a therapeutic agent that is at least partially encapsulated in a liposome comprising an amount of at least one poloxamer, 1,2-distearoyl-sn-glycero-3-phosphocholine (DSPC), 1,2-Dipalmitoyl-sn-glycero-3-phosphocholine (DPPC), and a polyethylene glycol (PEG).

In some aspects provided herein are methods of treating or preventing a cardiovascular-related disease in a subject in need thereof, the method comprising administering a therapeutically effective amount of the composition according to an embodiment of the present disclosure.

In some aspects provided herein are methods of preparing the composition according to an embodiment of the present disclosure comprising dissolving the DSPC and the DPPC in ethanol and sonicating until dissolved to form a first composition; dissolving the PEG and the poloxamer in methanol and sonicating until dissolved to form a second composition; forming a lipid film from the first composition and the second composition; and mixing the therapeutic agent with the lipid film to form a liposome.

In some aspects provided herein are kits that comprise a composition according to an embodiment of the present disclosure and instructions for treating or preventing a cardiovascular-related disease or disorder.

In some embodiments, the therapeutic agent is an apelin peptide.

In some embodiments, the at least one poloxamer is poloxamer 124, poloxamer 181, poloxamer 184, poloxamer 188, poloxamer 331, and poloxamer 407, or any combination thereof.

In some embodiments, the PEG has an average molecular weight of from about 200 to about 20000 daltons (PEG 200 to PEG 20000), for example, PEG 8000.

In some embodiments, the apelin peptide comprises between about 15 wt % and about 60 wt %. In some embodiments, the poloxamer comprises between about 1 wt % and about 20 wt %. In some embodiments, the DSPC comprises between about 5 wt % and about 30 wt %. In some embodiments, the DPPC comprises between about 5 wt % and about 30 wt %. In some embodiments, the PEG comprises between about 10 wt % and about 20 wt %.

In some embodiments, the composition further comprises cholesterol. In some embodiments, the cholesterol comprises between about 1 wt % and about 10 wt %.

In some embodiments, the composition further comprises a pharmaceutically acceptable excipient. In some embodiments, the composition further comprises at least one additional therapeutic agent, for example, an angiotensin-converting enzyme (ACE) inhibitor, relaxin, a natriuretic peptide, ghrelin, or other bioactive peptides.

In some embodiments, the composition comprises about 25 wt % of an apelin peptide, about 17 wt % poloxamer 188, about 25 wt % DSPC, about 25 wt % DPPC, and about 8 wt % PEG 8000. In other embodiments, the composition comprises about 45 wt % of an apelin peptide, about 15 wt % poloxamer 188, about 10 wt % DSPC, about 10 wt % DPPC, about 15 wt % PEG 8000, and about 5 wt % cholesterol.

In some embodiments, the cardiovascular-related disease is pulmonary hypertension, heart failure, myocardial infarction, diabetic nephropathy, chronic kidney disease, acute kidney disease, erectile dysfunction, diabetes, or a metabolic-related disorder.

In some embodiments, the composition is administered intravenously, subcutaneously, orally, or via inhalation.

In some embodiments, the liposome is lyophilized.

BRIEF DESCRIPTION OF THE DRAWINGS

Many aspects of the present disclosure can be better understood with reference to the following drawings.

FIGS. 9A-9D shows representative bioactive peptides.

DETAILED DESCRIPTION

Figure 1:
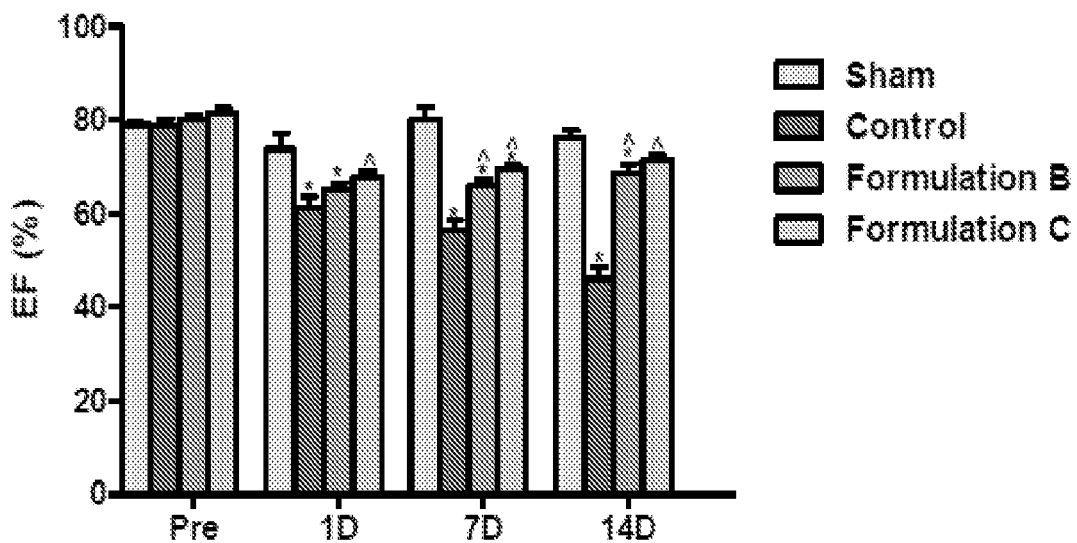
FIGS. 1A and 1B show changes in ejection fraction (EF) before surgery and 1 day-, 7 days-, and 14 days-after surgery with weekly administration (two weeks; on day 1 and day 7) of sham (PBS), control (no apelin), Formulation B (apelin only), or Formulation C (apelin liposome).
Figure 1:
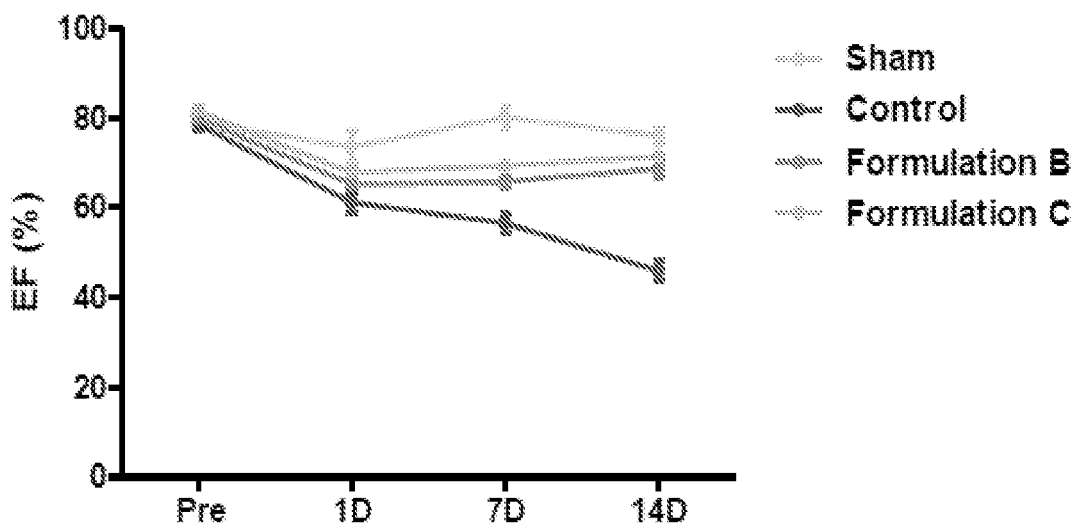

The present disclosure is directed to methods for treating cardiovascular-related diseases and compositions for use in these methods.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

It must be noted that as used herein and in the appended claims, the singular forms "a", "an", and "the" include plural referents unless the context clearly dictates otherwise. Thus, for example, reference to "a liposome" includes a plurality of liposome.

As used herein the following terms have the following meanings.

The term "about" when used before a numerical designation, e.g., temperature, time, amount, concentration, and such other, including a range, indicates approximations which may vary by (+) or (−) 20%, 10%, 5% or 1%.

Also as used herein, "and/or" refers to and encompasses any and all possible combinations of one or more of the associated listed items, as well as the lack of combinations when interpreted in the alternative ("or").

The terms "administering," "administer" and the like refer to introducing an agent (e.g., apelin) into a subject. Typically, an effective amount is administered, which amount can be determined by the treating physician or the like. Any route of administration, such as topical, subcutaneous, peritoneal, intravenous, intraarterial, inhalation, vaginal, rectal, buccal, introduction into the cerebrospinal fluid, or instillation into body compartments can be used. The terms and phrases "administering" and "administration of," when used in connection with a composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer an agent (e.g., apelin) and/or provides a patient with a prescription for a drug is administering the agent to the patient. "Periodic administration" or "periodically administering" refers to multiple treatments that occur on a daily, weekly, or a monthly basis. Periodic administration may also refer to administration of an agent one, two, three or more time(s) per day.

An "effective amount" is an amount of an agent or compound (e.g., apelin) sufficient to effect beneficial or desired results. An effective amount can be in one or more administrations, applications or dosages. Determination of these parameters is well within the skill of the art. These considerations, as well as effective formulations and administration procedures are well known in the art and are described in standard textbooks.

A "subject," "individual" or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets.

The term "sequence identity" with respect to a protein or amino acid sequence (or a DNA or RNA sequence) refers to the percentage of amino acid residues (or nucleotide residues) in a candidate sequence that are identical to the amino acid residues in the specific protein or amino acid sequence (or nucleotide residues in the specific DNA or RNA sequence), after aligning the sequences and introducing gaps, if necessary, to achieve a maximum percent sequence identity, and not considering any conservative substitutions as part of the sequence identity. Alignment can be achieved by any method known to one of skill in the art, for example, by using publicly available programs such as BLAST and EMBOSS. Those skilled in the art can determine appropriate parameters for measuring alignment, including any algorithms needed to achieve maximal alignment over the full length of the sequences being compared.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Compositions and Formulations

Provided herein are compositions and formulations that comprise at least one therapeutic agent that is at least partially encapsulated in a liposome.

In some embodiments, the therapeutic agent is an apelin peptide. In some embodiments, the apelin peptide comprises an amino acid sequence selected from the group consisting of SEQ ID NOS: 1-7 as set forth in Table 1 below, or a sequence having at least about 60%, about 65%, about 70%, about 75%, about 80%, about 85%, about 90%, about 95%, about 96%, about 97%, about 98%, about 99%, or 100% sequence identity thereto. Non-limiting examples of suitable apelin peptide isoforms include apelin-12, apelin-13, pyroglutamyl apelin-13 ([Pyr1]-apelin-13]), apelin 17, apelin-19, and apelin 36. In some embodiments, the apelin peptide is pyroglutamyl apelin-13. Suitable apelin peptides and biologically active variants are described in U.S. Patent Publ. No. 2016/0058705, which is incorporated by reference in its entirety.

TABLE 1

Apelin peptide sequences

| SEQ ID NO. | Sequence |
|---|---|
| 1 (apelin pre-protein) | Met Asn Leu Arg Leu Cys Val Gln Ala Leu Leu Leu Leu Trp Leu Ser Leu Thr Ala Val Cys Gly Gly Ser Leu Met Pro Leu Pro Asp Gly Asn Gly Leu Glu Asp Gly Asn Val Arg His Leu Val Gln Pro Arg Gly Ser Arg Asn Gly Pro Gly Pro Trp Gln Gly Gly Arg Arg Lys Phe Arg Arg Gln Arg Pro Arg Leu Ser His Lys Gly Pro Met Pro Phe (MNLRLCVQALLLLWLSLTAVCGGSLMPLPDGNGLEDGNVRHL VQPRGSRNGPGPWQGGRRKFRRQRPRLSHKGPMPF) |
| 2 (apelin-12) | Arg Pro Arg Leu Ser His Lys Gly Pro Met Pro Phe (RPRLSHKGPMPF) |
| 3 (apelin-13) | Gln Arg Pro Arg Leu Ser His Lys Gly Pro Met Pro Phe (QRPRLSHKGPMPF) |
| 4 ([Pyr1]-apelin-13) | Xaa Arg Pro Arg Leu Ser His Lys Gly Pro Met Pro Phe (XRPRLSHKGPMPF) (Xaa/X is pyroglutamate) |
| 5 (apelin-17) | Lys Phe Arg Arg Gln Arg Pro Arg Leu Ser His Lys Gly Pro Met Pro Phe (KFRRQRPRLSHKGPMPF) |
| 6 (apelin-19) | Arg Arg Lys Phe Arg Arg Gln Arg Pro Arg Leu Ser His Lys Gly Pro Met Pro Phe (RRKFRRQRPRLSHKGPMPF) |
| 7 (apelin-36) | Leu Val Gln Pro Arg Gly Ser Arg Asn Gly Pro Gly Pro Trp Gln Gly Gly Arg Arg Lys Phe Arg Arg Gln Arg Pro Arg Leu Ser His Lys Gly Pro Met Pro Phe (LVQPRGSRNGPGPWQGGRRKFRRQRPRLSHKGPMPF) |

In some embodiments, the therapeutic agent (e.g., an apelin peptide) and/or at least one additional therapeutic agent comprises between about 15 wt % and about 60 wt %.

In some embodiments, the therapeutic agent comprises between about 5 wt % and about 30 wt %, about 10 wt % and about 25 wt %, or about 15 wt % and about 20%. In some embodiments, the therapeutic agent comprises about 5 wt %, about 10 wt %, about 15 wt %, about 20 wt %, about 21 wt %, about 22 wt %, about 23 wt %, about 24 wt %, about 25 wt %, about 26 wt %, about 27 wt %, about 28 wt %, about 29 wt %, or about 30 wt %. In some embodiments, the therapeutic agent comprises less than about 30 wt %, less than about 29 wt %, less than about 28 wt %, less than about 27 wt %, less than about 26 wt %, less than about 25 wt %, less than about 24 wt %, less than about 23 wt %, less than about 22 wt %, less than about 21 wt %, less than about 20 wt %, less than about 19 wt %, less than about 18 wt %, less than about 17 wt %, less than about 16 wt %, less than about 15 wt %, less than about 14 wt %, less than about 13 wt %, less than about 12 wt %, less than about 11 wt %, less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, or less than about 1 wt %.

In some embodiments, the therapeutic agent comprises between about 35 wt % and about 60 wt %, about 35 wt % and about 55 wt %, about 35 wt % and about 50%, about 35 wt % and about 45%, or about 35 wt % and about 40%. In some embodiments, the therapeutic agent comprises between about 40 wt % and about 60 wt %, about 40 wt % and about 55 wt %, about 40 wt % and about 50%, or about 40 wt % and about 45%. In some embodiments, the therapeutic agent comprises about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49%, about 50 wt %, about 51 wt %, about 52 wt %, about 53 wt %, about 54 wt %, about 55 wt %, about 56 wt %, about 57 wt %, about 58 wt %, about 59%, or about 60 wt %. In some embodiments, the therapeutic agent comprises more than about 35 wt %, more than about 36 wt %, more than about 37 wt %, more than about 38 wt %, more than about 39 wt %, more than about 40 wt %, more than about 41 wt %, more than about 42 wt %, more than about 43 wt %, more than about 44 wt %, more than about 45 wt %, more than about 46 wt %, more than about 47 wt %, more than about 48 wt %, more than about 49 wt %, more than about 50 wt %, more than about 51 wt %, more than about 52 wt %, more than about 53 wt %, more than about 54 wt %, more than about 55 wt %, more than about 56 wt %, more than about 57 wt %, more than about 58 wt %, more than about 59 wt %, or more than about 60 wt %.

In some embodiments, the therapeutic agent is at least partially encapsulated in a liposome comprising an amount of at least one poloxamer, at least one lipid, and a polyethylene glycol (PEG).

Non-limiting examples of suitable poloxamers include poloxamer 124, poloxamer 181, poloxamer 184, poloxamer 188, poloxamer 331, and poloxamer 407, or any combination thereof. In some embodiments, the poloxamer is poloxamer 188.

In some embodiments, the poloxamer (e.g., poloxamer 188) comprises between about 1 wt % and about 20 wt %.

In some embodiments, the poloxamer comprises between about 1 wt % and about 14 wt %, about 2 wt % and about 12 wt %, about 4 wt % and about 10%, or about 6 wt % and about 8%. In some embodiments, the poloxamer comprises about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, or about 14 wt %. In some embodiments, the poloxamer comprises less than about 14 wt %, less than about 13 wt %, less than about 12 wt %, less than about 11 wt %, less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, or less than about 1 wt %.

In some embodiments, the poloxamer comprises between about 12 wt % and about 20 wt %, about 12 wt % and about 18 wt %, about 12 wt % and about 16%, or about 12 wt % and about 14%. In some embodiments, the poloxamer comprises about 12 wt %, about 13 wt %, about 14 wt %, about 15 wt %, about 16 wt %, about 17 wt %, about 18 wt %, about 19 wt %, or about 20 wt %. In some embodiments, the poloxamer comprises more than about 12 wt %, more than about 13 wt %, more than about 14 wt %, more than about 15 wt %, more than about 16 wt %, more than about 17 wt %, more than about 18 wt %, more than about 19 wt %, or more than about 20 wt %.

In some embodiments, the at least one lipid (e.g., 1,2-Distearoyl-sn-glycero-3-phosphocholine (DPSC) and/or 1,2-Dipalmitoyl-sn-glycero-3-phosphocholine (DPPC)) comprises between about 5 wt % and about 30 wt %. Non-limiting examples of suitable lipids include Soybean phosphatidylcholine (SPC), Hydrogenated soybean phosphatidylcholine (HSPC), Egg sphingomyelin (ESM), Egg phosphatidylcholine (EPC), Dimyristoyl phosphatidylcholine (DMPC), Dipalmitoyl phosphatidylcholine (DPPC), Dioleoyl phosphatidylcholine (DOPC), Dimyristoyl phosphatidylglycerol (DMPG), Dipalmitoyl phosphatidylglycerol (DPPG), Dioleoyl phosphatidylglycerol (DOPG), Dimyristoyl phosphatidylethanolamine (DMPE), Dipalmitoyl phosphatidylethanolamine (DPPE), Dioleoyl phosphatidylethanolamine (DOPE), Dimyristoyl phosphatidylserine (DMPS), Dipalmitoyl phosphatidylserine (DPPS), Dioleoyl phosphatidylserine (DOPS).

In some embodiments, the DSPC comprises between about 20 wt % and about 30 wt %, about 22 wt % and about 28 wt %, or about 24 wt % and about 26%. In some embodiments, the DSPC comprises about 20 wt %, about 21 wt %, about 22 wt %, about 23 wt %, about 24 wt %, about 25 wt %, about 26 wt %, about 27 wt %, about 28 wt %, about 29 wt %, or about 30 wt %. In some embodiments, the DSPC comprises more than about 20 wt %, more than about 21 wt %, more than about 22 wt %, more than about 23 wt %, more than about 24 wt %, more than about 25 wt %, more than about 26 wt %, more than about 27 wt %, more than about 28 wt %, more than about 29 wt %, or more than about 30 wt %.

In some embodiments, the DSPC comprises between about 5 wt % and about 15 wt %, about 7 wt % and about 13 wt %, or about 9 wt % and about 11%. In some embodiments, the DSPC comprises about 5 wt %, about 6 wt %, about 7 wt %, about 8 wt %, about 9 wt %, about 10 wt %, about 11 wt %, about 12 wt %, about 13 wt %, about 14 wt %, or about 15 wt %. In some embodiments, the DSPC comprises less than about 15 wt %, less than about 14 wt %, less than about 13 wt %, less than about 12 wt %, less than about 11 wt %, less than about 10 wt %, less than about 9 wt %, less than about 8 wt %, less than about 7 wt %, less than about 6 wt %, or less than about 5 wt %.

In some embodiments, the DPPC comprises between about 5 wt % and about 30 wt %.

In some embodiments, the DPPC comprises between about 20 wt % and about 30 wt %, about 22 wt % and about 28 wt %, or about 24 wt % and about 26%. In some embodiments, the DPPC comprises about 20 wt %, about 21 wt %, about 22 wt %, about 23 wt %, about 24 wt %, about 25 wt %, about 26 wt %, about 27 wt %, about 28 wt %, about 29 wt %, or about 30 wt %. In some embodiments, the DPPC comprises more than about 20 wt %, more than about 21 wt %, more than about 22 wt %, more than about 23 wt %, more than about 24 wt %, more than about 25 wt %, more than about 26 wt %, more than about 27 wt %, more than about 28 wt %, more than about 29 wt %, or more than about 30 wt %.

In some embodiments, the DPPC comprises between about 5 wt % and about 15 wt %, about 7 wt % and about 13 wt %, or about 9 wt % and about 11%. In some embodiments, the DPPC comprises about 5 wt %, about 6 wt %, about 7 wt %, about 8 wt %, about 9 wt %, about 10 wt %, about 11 wt %, about 12 wt %, about 13 wt %, about 14 wt %, or about 15 wt %. In some embodiments, the DPPC comprises less than about 15 wt %, less than about 14 wt %, less than about 13 wt %, less than about 12 wt %, less than about 11 wt %, less than about 10 wt %, less than about 9 wt %, less than about 8 wt %, less than about 7 wt %, less than about 6 wt %, or less than about 5 wt %.

In some embodiments, the PEG has an average molecular weight of from about 200 to about 20000 daltons. Non-limiting examples of suitable PEG include PEG 200, PEG 300, PEG 400, PEG 1000, PEG 1540, PEG 4000, PEG 5000, PEG 6000, PEG 7000, PEG 8000, PEG 9000, or PEG 10000. In some embodiments, the PEG is PEG 8000. In some embodiments, the PEG comprises between about 10 wt % and about 20 wt %, about 12 wt % and about 18 wt %, about 12 wt % and about 16%, or about 12 wt % and about 14%. In some embodiments, the PEG comprises about 10 wt %, about 11 wt %, about 12 wt %, about 13 wt %, about 14 wt %, about 15 wt %, about 16 wt %, about 17 wt %, about 18 wt %, about 19 wt %, or about 20 wt %. In some embodiments, the poloxamer comprises more than about 10 wt %, more than about 11 wt %, more than about 12 wt %, more than about 13 wt %, more than about 14 wt %, more than about 15 wt %, more than about 16 wt %, more than about 17 wt %, more than about 18 wt %, more than about 19 wt %, or more than about 20 wt %. In some embodiments, the PEG comprises less than about 20 wt %, less than about 19 wt %, less than about 18 wt %, less than about 17 wt %, less than about 16 wt %, less than about 15 wt %, less than about 14 wt %, less than about 13 wt %, less than about 12 wt %, less than about 11 wt %, or less than about 10 wt %.

In some embodiments, composition further comprises cholesterol. In some embodiments, the cholesterol comprises between about 1 wt % and about 10 wt %, about 2 wt % and about 8 wt %, or about 4 wt % and about 6%. In some embodiments, the cholesterol comprises about 1 wt %, about 2 wt %, about 3 wt %, about 4 wt %, about 5 wt %, about 6 wt %, about 7 wt %, about 8 wt %, about 9 wt %, or about 10 wt %. In some embodiments, the poloxamer comprises less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, or less than about 1 wt %.

In some embodiments, the composition comprises a therapeutic agent (e.g., apelin) in an amount of between about 5 wt % and about 30 wt %, about 10 wt % and about 25 wt %, or about 15 wt % and about 20%; a poloxamer (e.g., poloxamer 188) in an amount of between about 1 wt % and about 14 wt %, about 2 wt % and about 12 wt %, about 4 wt % and about 10%, or about 6 wt % and about 8%; DSPC in an amount of between about 20 wt % and about 30 wt %, about 22 wt % and about 28 wt %, or about 24 wt % and about 26%; DPPC in an amount of between about 20 wt % and about 30 wt %, about 22 wt % and about 28 wt %, or about 24 wt % and about 26%; and PEG (e.g., PEG 8000) in an amount of between about 10 wt % and about 20 wt %, about 12 wt % and about 18 wt %, about 12 wt % and about 16%, or about 12 wt % and about 14%. In some embodiments, the composition comprises about 25 wt % of an apelin peptide, about 17 wt % poloxamer 188, about 25 wt % DSPC, about 25 wt % DPPC, and about 8 wt % PEG 8000.

In some embodiments, the composition comprises a therapeutic agent (e.g., apelin) in an amount of between about 35 wt % and about 60 wt %, about 35 wt % and about 55 wt %, about 35 wt % and about 50%, about 35 wt % and about 45%, or about 35 wt % and about 40%; a poloxamer (e.g., poloxamer 188) in an amount of between about 12 wt % and about 20 wt %, about 12 wt % and about 18 wt %, about 12 wt % and about 16%, or about 12 wt % and about 14%; DSPC in an amount of between about 5 wt % and about 15 wt %, about 7 wt % and about 13 wt %, or about 9 wt % and about 11%; DPPC in an amount of between about 5 wt % and about 15 wt %, about 7 wt % and about 13 wt %, or about 9 wt % and about 11%; PEG (e.g., PEG 8000) in an amount of between about 10 wt % and about 20 wt %, about 12 wt % and about 18 wt %, about 12 wt % and about 16%, or about 12 wt % and about 14%; and cholesterol in an amount of between about 1 wt % and about 10 wt %, about 2 wt % and about 8 wt %, or about 4 wt % and about 6%. In some embodiments, the composition comprises about 45 wt % of an apelin peptide, about 15 wt % poloxamer 188, about 10 wt % DSPC, about 10 wt % DPPC, about 15 wt % PEG 8000, and about 5 wt % cholesterol.

In some embodiments, the composition comprises a therapeutic agent (e.g., an apelin peptide) and a poloxamer (e.g., poloxamer 188).

In one embodiment, the composition is "Formulation 1" as set forth below. In another embodiment, the composition is "Formulation 2" as set forth below. In other embodiments, the composition comprises the same components and weight %'s as Formulation 1 or 2, but with different weights.

TABLE 2

Formulation 1 and Formulation 2

| | Formulation 1 | | Formulation 2 | |
|---|---|---|---|---|
| | Weight (mg) | Weight % | Weight (mg) | Weight % |
| DSPC | 450 | 25.00% | 100 | 10.00% |
| DPPC | 450 | 25.00% | 100 | 10.00% |
| Poloxamer 188 | 150 | 8.33% | 150 | 15.00% |
| PEG 8000 | 300 | 16.67% | 150 | 15.00% |
| [Pyr1]-Apelin-13 | 450 | 25.00% | 450 | 45.00% |
| Cholesterol | — | — | 50 | 5.00% |
| TOTAL | 1800 | 100.00% | 1000 | 100.00% |

In some embodiments, the composition further comprises at least one additional therapeutic agent. Suitable additional therapeutic agents include inotropes, beta adrenergic receptor blockers, HMG-Co-A reductase inhibitors, angiotensin II receptor antagonists, angiotensin converting enzyme (ACE) inhibitors, calcium channel blockers (CCB), endothelin antagonists, renin inhibitors, diuretics, ApoA-1 mimetics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor. In some embodiments, the additional therapeutic agent is an ACE inhibitor, relaxin, a natriuretic peptide, ghrelin, or other bioactive peptides. Non-limiting examples of suitable bioactive peptides include any one of the bioactive peptides in FIGS. 9A-D (see also, e.g., Erdmann 2008; Chakrabarti 2016).

In one embodiment, the additional therapeutic agent is selected from inotropes, beta adrenergic receptor blockers, HMG-Co-A reductase inhibitors, angiotensin II receptor antagonists, angiotensin converting enzyme (ACE) inhibitors, calcium channel blockers (CCB), endothelin antagonists, renin inhibitors, diuretics, ApoA-1 mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide), a NEP inhibitor, and angiotensin converting enzyme-2 (ACE-2). The term "in combination with" a second agent or treatment includes co-administration of the composition disclosed and described herein (e.g., apelin liposome) with the second agent or treatment, administration of the composition disclosed and described herein, followed by the second agent or treatment and administration of the second agent or treatment first, followed by the composition disclosed and described herein. Inotropes as used herein include for example dobutamine, isoproterenol, milrinone, amirinone, levosimendan, epinephrine, norepinephrine, isoproterenol and digoxin. Beta adrenergic receptor blockers as used herein include for example acebutolol, atenolol, betaxolol, bisoprolol, carteolol, metoprolol, nadolol, propranolol, sotalol and timolol. Anti-coagulants as used herein include Dalteparin, Danaparoid, Enoxaparin, Heparin, Tinzaparin, and Warfarin. The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rosuvastatin, rivastatin, simvastatin, velostatin, and pharmaceutically acceptable salts thereof. The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, zofenopril, or pharmaceutically acceptable salt thereof. The term "endothelin antagonist" includes bosentan, tezosentan, and pharmaceutically acceptable salts thereof. Additional examples of acceptable additional therapeutic agents are in PCT Publ. No. WO/2013/111110 which is incorporated by references in its entirety along with references cited therein.

In some embodiments, the additional therapeutic agent comprises valsartan, candesartan, or losartan.

In some embodiments, the composition further comprises a pharmaceutically acceptable excipient, diluent, carrier, or any combination thereof. In some embodiments, the composition is soluble in the pharmaceutically acceptable excipient. In some embodiments, the composition is soluble in, and do not precipitate out of, the pharmaceutically acceptable excipient for a period of time from about 30 minutes, about 1 hour, about 2 hours, about 3 hours, about 4 hours, about 5 hours, about 6 hours, about 12 hours, about 1 day, about 2 days, about 3 days, about 4 days, about 5 day, about 6 days, about 1 week, about 2 weeks, about 3 weeks, about a month, or longer.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Compositions may be prepared using conventional techniques that may include sterile isotonic saline, water, 1,3-butanediol, ethanol, 1,2-propylene glycol, polyglycols mixed with water, Ringer's solution, etc. In one embodiment, a coloring agent is added to facilitate in locating and properly placing the composition to the intended treatment site.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

To control tonicity, the composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

The composition can be included in an implantable device. Suitable implantable devices contemplated by this invention include intravascular stents (e.g., self-expandable stents, balloon-expandable stents, and stent-grafts), scaffolds, grafts, and the like. Such implantable devices can be coated on at least one surface, or impregnated, with a composition according to an embodiment disclosed and described herein.

Methods of Treatment

Provided herein are methods treating or preventing a cardiovascular-related disease in a subject in need thereof. In some embodiments, the methods comprise administering a therapeutically effective amount of a composition disclosed and described herein to the subject.

Non-limiting examples of suitable cardiovascular-related diseases include cardiac diseases, vascular diseases, and metabolic diseases. Other suitable conditions useful for treatment with the compositions disclosed and described herein include water retention and burn injuries. Non-limiting examples of cardiac diseases include Chronic Heart Failure, Acute Decompensated Heart Failure, Post-Myocardial Infarction, Atrial Fibrillation, Brugada Syndrome, Ventricular Tachycardia, Atherosclerosis, Ischemic Cardiovascular Disease, Cardiomyopathy, Cardiac Fibrosis, Cardiac Ischemia/Reperfusion Injury, Arrhythmia, and Amyloidosis. Non-limiting examples of vascular diseases include Hypertension, Resistant Hypertension, Pulmonary Hypertension, Peripheral Arterial Disease, Erectile Dysfunction, Restenosis, and Preeclampsia. Non-limiting examples of metabolic diseases include Type 2 Diabetes, Type 1 Diabetes, Diabetic Nephropathy, Diabetic Retinopathy, Chronic Kidney Disease, Acute Kidney Disease, Renal Fibrosis, Renal Ischemia/Reperfusion Injury, Polycystic Kidney Disease, Hemodialysis, and Obesity.

In some embodiments, the cardiovascular-related disease is selected from the group consisting of pulmonary hypertension, heart failure, myocardial infarction, diabetic nephropathy, chronic kidney disease, acute kidney disease, erectile dysfunction, diabetes, and metabolic-related disorders.

The compositions can be administered to a subject by any suitable mode and route. Non-limiting examples include internal, pulmonary, rectal, vaginal, lingual, intravenous, intraarterial, intramuscular, intraperitoneal, intracutaneous and subcutaneous routes. In some embodiments, the composition is administered intravenously or subcutaneously. Compositions may also be suitable for transdermal delivery as part of a cream, gel, or patch. Other dosage forms include tablets, capsules, pills, powders, aerosols, suppositories, parenterals, and oral liquids, including suspensions, solutions and emulsions. Sustained- or accelerated-release dosage forms may also be used.

In one embodiment, a subject with a cardiovascular-related disease is administered a therapeutically effective amount of a composition comprising DSPC in an amount of about 25 wt %, in an amount of about 25 wt % DPPC, Poloxamer 188 in an amount of about 8.33 wt %, PEG 8000 in an amount of about 16.67 wt %, and [Pyr1]-Apelin-13 in an amount of about 25 wt %.

In one embodiment, a subject with a cardiovascular-related disease is administered a therapeutically effective amount of a composition comprising DSPC in an amount of about 10 wt %, DPPC in an amount of about 10 wt %, Poloxamer 188 in an amount of about 15 wt %, PEG 8000 in an amount of about 15 wt %, [Pyr1]-Apelin-13 in an amount of about 45 wt %, and cholesterol in an amount of about 5 wt %.

In one embodiment, a subject with a cardiovascular-related disease is administered intravenously, subcutaneously, orally, or via inhalation a therapeutically effective amount of a composition comprising DSPC in an amount of about 25 wt %, in an amount of about 25 wt % DPPC, Poloxamer 188 in an amount of about 8.33 wt %, PEG 8000 in an amount of about 16.67 wt %, and [Pyr1]-Apelin-13 in an amount of about 25 wt %.

In one embodiment, a subject with a cardiovascular-related disease is administered intravenously, subcutaneously, orally, or via inhalation a therapeutically effective amount of a composition comprising DSPC in an amount of about 10 wt %, DPPC in an amount of about 10 wt %, Poloxamer 188 in an amount of about 15 wt %, PEG 8000 in an amount of about 15 wt %, [Pyr1]-Apelin-13 in an amount of about 45 wt %, and cholesterol in an amount of about 5 wt %.

In one embodiment, a composition of the disclosure is administered to a subject in an amount sufficient to provide a daily dose of the therapeutic agent about 1 mg to about 10,000 mg, about 25 mg to about 5000 mg, about 50 mg to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In one embodiment, a composition of the disclosure is administered to a subject in an amount sufficient to provide a weekly and/or biweekly dose of the therapeutic agent about 1 mg to about 10,000 mg, about 25 mg to about 5000 mg, about 50 mg to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In one embodiment, a composition of the disclosure is administered to a subject in an amount sufficient to provide a monthly dose of the therapeutic agent about 1 mg to about 10,000 mg, about 25 mg to about 5000 mg, about 50 mg to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

EXAMPLES

Example 1: Pharmacodynamics of Apelin Formulations in Mouse Model of Myocardial Hypertrophy and Heart Failure Animals. C57BL/6J mice between 6 to 8 weeks and 8 to 10 weeks of age were used as a pharmacodynamic animal model of traverse aortic constriction (TAC)-induced cardiac hypertrophy and heart failure. Mice were grouped accordingly to treatment groups as set out in Table 3 below. Mice received intraperitoneal injections of either 100 µL PBS (Sham group), excipient (liposome) only Control group, apelin only (Formulation B group), or apelin liposome (Formulation C group).

TABLE 3

Mouse treatment groups

| Treatment Group | Number of animals |
|---|---|
| Sham group | 6 |
| Control group-liposome only | 6 |
| Formulation B group-apelin only | 7 |
| Formulation C only-apelin liposome | 7 |

TAC Surgical Procedures.

The surgical area was disinfected for binocular stereoscopic operation. Incisions were made to reveal the heart and left atrial appendage. The aortic arch area between the free-head arm stem and the left common carotid artery was then carefully observed under a stereomicroscope. The aorta was placed on the 4-gauge needle (0.4 mm in diameter) between the head arm stem and the left common carotid artery resulting in aortic stenosis. Surgical sites were sutured and mice observed for normal thorax undulation. Mice were randomly divided into the four group outlined in the table above. Briefly, the Control group (intraperitoneal injection of blank excipients without drugs), Formulation B group (apelin only), Formulation C group (apelin liposome); the other group is the Sham group with the corresponding surgical operation of mice but no narrowing of the aorta.

Evaluation of Echocardiographic Function.

Mice were evaluated 1 hour before the first dose, 1 hour after the first dose and at 1 week and 2 weeks after the operation. Briefly, M-mode echocardiography was used to detect the changes of cardiac function in postoperative mice. The changes of left ventricular anterior and posterior wall were recorded by M-mode ultrasound with 2D image. M-curves show the location and dynamics of the endocardium to measure the end of systolic and diastolic left ventricular anteroposterior diameter size. The left ventricular systolic diameter (LVIDs), left ventricular end diastolic diameter (LVIDd), left ventricular ejection fraction (EF), left ventricular fractional shortening (FS), left ventricular posterior wall thickness (LVPWd) were calculated and other parameters were measured.

Pathological Evaluation.

At the end of the study, animals were sacrificed and thoracotomies were performed to remove the heart. Hearts were rinsed in normal saline and fixed in fresh 4% paraformaldehyde. Samples were paraffin embedded after being treated with Masson staining and microscopic observations were performed. A similar procedure was performed with HE staining. Evaluation indicators: pathological description, the main study on hypertrophy.

Statistical Analysis.

The experimental data of each group were described by mean±standard deviation. One-way ANOVA was used to compare the differences between normal and variance groups. LSD test was used to compare the differences between the two groups. The Kruskal-Wallis H test (KW) was used to test the difference between the two groups and the normal distribution or variance. The Mann-Whitney U method was used for multiple comparisons between groups. $p<0.05$ for the difference was statistically significant. All statistical analyses were performed using SPSS 22.0 for Windows software.

Following the methods described above ultrasound-guided M-mode ultrasonography was used to measure the EF, FS, LVIDs, LVIDd and LVPWd of the left ventricle of the sternum in order to determine the changes of cardiac function.

Ejection fraction (EF) is the fraction of blood ejected from a ventricle of the heart with each heartbeat. EF is calculated by dividing the stroke volume by the end-diastolic volume and is an inherent volumetric measure of the pumping efficiency of the heart. Ejection fraction is an important indicator of cardiac function. As shown in FIGS. 1A and 1B, one day (1 D) after surgery, the Sham group had EF values slightly reduced, presumably due to thoracic injury; but at seven days after surgery (7 D), the EF value had been restored and was then maintained at relatively stable state. In the Control group, the EF value continued to decrease after 7 days and the decline was more severe after 7 days. It is presumed that the cardiac injury occurred immediately after the aortic constriction and the compensatory effect of 7 D after injury is more obvious with follow-up injury continuing. In the two administration groups, the decrease in EF level was mitigated slowly after 1 D.

Figure 2:
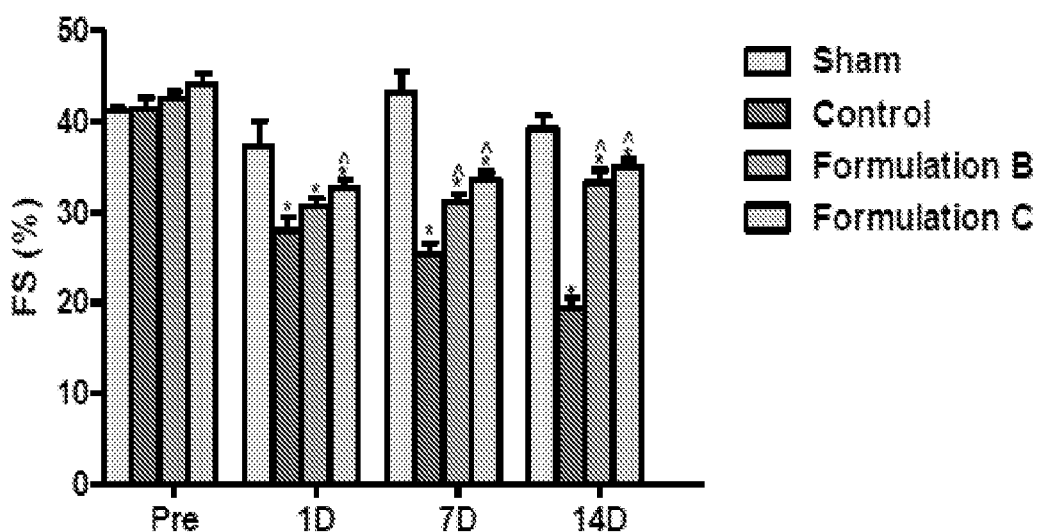
FIGS. 2A and 2B show changes in left ventricular shortening fraction (FS) before surgery and 1 day-, 7 days-, and 14 days-after surgery with weekly administration (two weeks; on day 1 and day 7) of sham (PBS), control (no apelin), Formulation B (apelin only), or Formulation C (apelin liposome).
Figure 2:
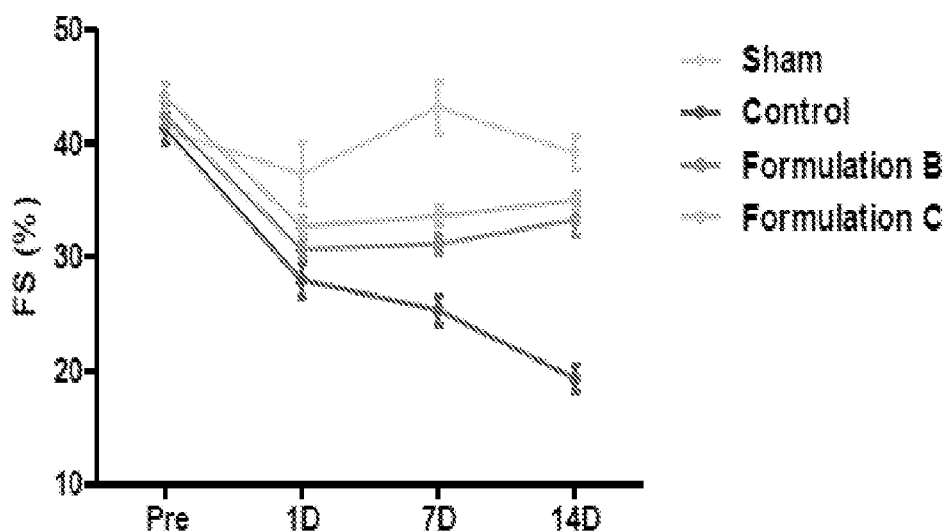
Figure 3:
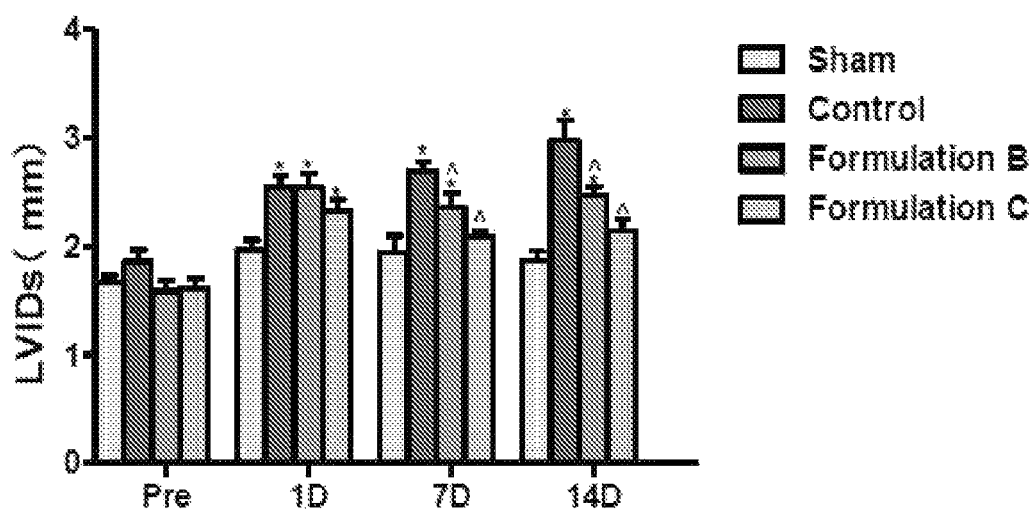
FIGS. 3A and 3B show changes in left ventricular systolic diameter (LVIDs) before surgery and 1 day-, 7 days-, and 14 days-after surgery with weekly administration (two weeks; on day 1 and day 7) of sham (PBS), control (no apelin), Formulation B (apelin only), or Formulation C (apelin liposome).
Figure 3:
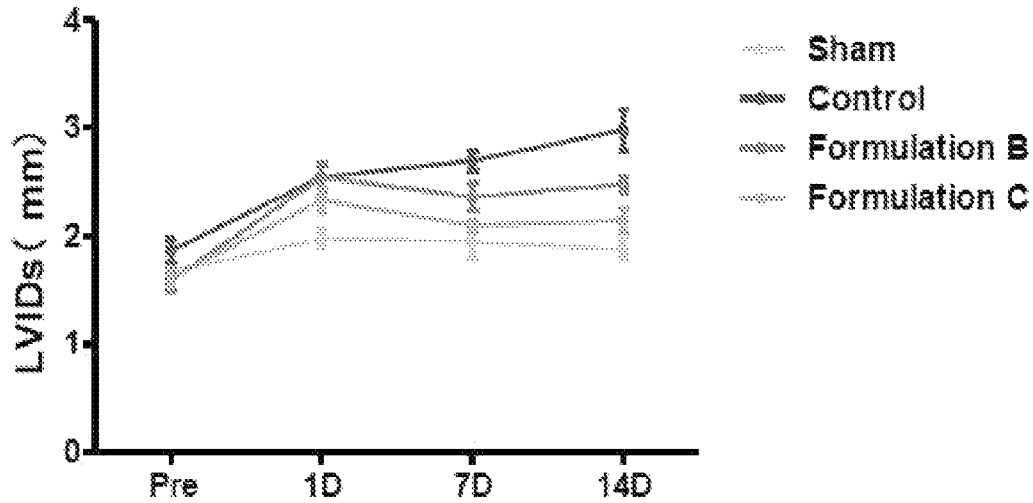

Left ventricular shortening fraction (FS) is similar to EF and is an important indicator of cardiac systolic function. As shown in FIGS. 2A and 2B, after 1 D the Sham group had a slightly reduced FS value, presumably due to thoracic injury. At 7 D, the FS value had been restored then maintained at stable state. In the Control group, the FS value continued to decrease after 7 D and the decline was more severe after 7 D. It is presumed that the cardiac injury occurred immediately after aortic constriction and the compensatory effect of 7 D after injury is more obvious with additional injury occurring. In the two administration groups, the decrease in FS level attenuated slowly after 1 D Left ventricular systolic diameter (LVIDs) changes can reflect cardiac remodeling. From FIGS. 3A and 3B, after 1 D, LVIDs of the Sham group were slightly increased, presumably due to thoracic injury. At 7 D, LVIDs had been restored then were maintained at stable state. The LVIDs of the Control group continued to increase after 7 days. It is presumed that the cardiac injury occurred immediately after aortic constriction and the compensatory effect of 7 D after injury is more obvious with additional injury occurring. For the two administration groups, increase in LVIDs was observed at 1 D postoperative, but this increase subsided through 14 D.

Figure 4:
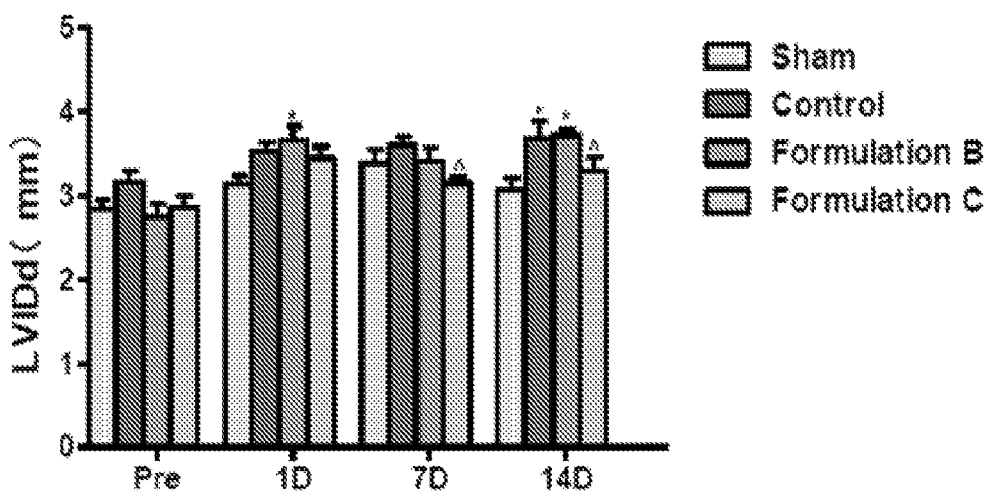
FIGS. 4A and 4B show changes in left ventricular diastolic diameter (LVIDd) before surgery and 1 day-, 7 days-, and 14 days-after surgery with weekly administration (two weeks; on day 1 and day 7) of sham (PBS), control (no apelin), Formulation B (apelin only), or Formulation C (apelin liposome).
Figure 4:
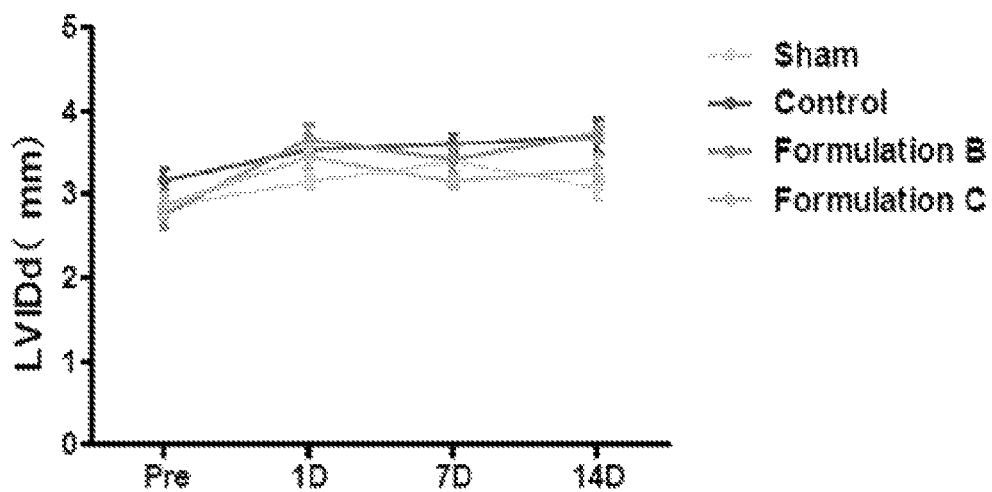

Left ventricular diastolic diameter (LVIDd) changes can reflect cardiac remodeling. As shown in FIGS. 4A and 4B, after 7 D, the LVIDd of the Sham group was slightly increased, presumably due to thoracic injury. After 7 D, this LVIDd began to decline. The LVIDd of the Control group increased continually after operation, suggesting that the injury occurred immediately after aortic constriction and further injury occurred. In the two administration groups, the LVIDd level increased at 1 D but this elevated level then subsided.

Figure 5:
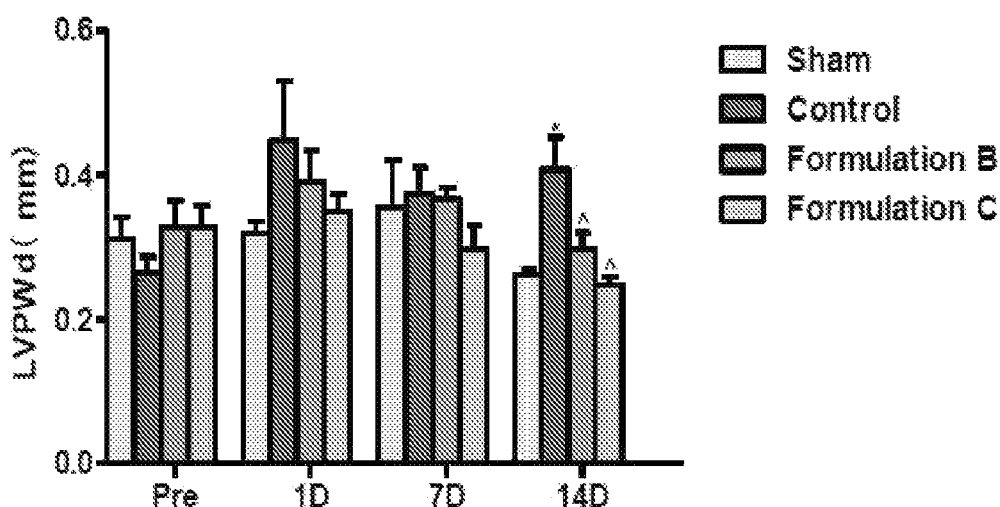
FIGS. 5A and 5B show changes in diastolic left ventricular posterior wall thickness (LVPWd) before surgery and 1 day-, 7 days-, and 14 days-after surgery with weekly administration (2 weeks; on day 1 and 7) of sham (PBS), control (no apelin), Formulation B (apelin only), or Formulation C (apelin liposome).
Figure 5:
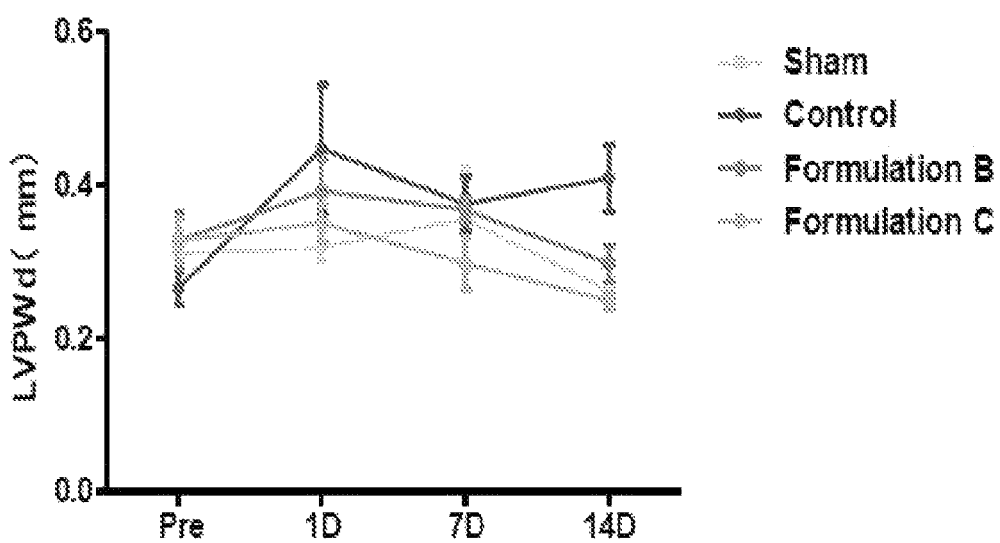

Left ventricular end diastolic wall thickness (LVPWd) changes can reflect cardiac remodeling. As shown in FIGS. 5A and 5B, after 1 D, the Sham group LVPWd value was relatively stable; this was slightly elevated at 7 D, presumably caused by thoracotomy injury. The LVPWd of the Control group increased after operation. In the two administration groups, the LVPWd increased at 1 D but the increase subsided afterwards.

Figure 6:
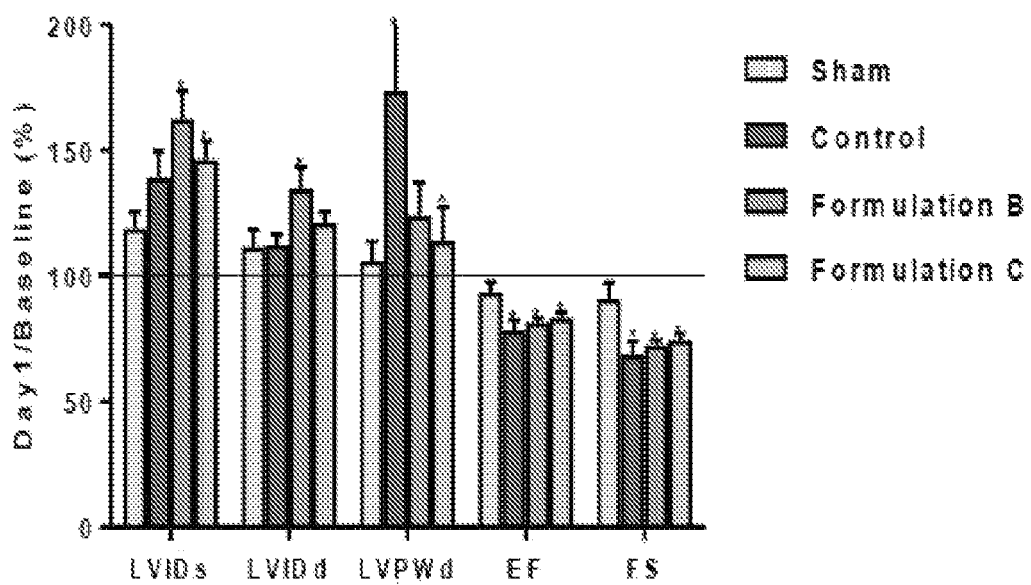
FIG. 6A shows Day 1 changes of cardiac ultrasonography (Day 1/Baseline (%)).
FIG. 6B shows Day 7 changes of cardiac ultrasonography (Day 7/Baseline (%)).
FIG. 6C shows Day 14 changes of cardiac ultrasonography (Day 14/Baseline (%)).
Figure 6:
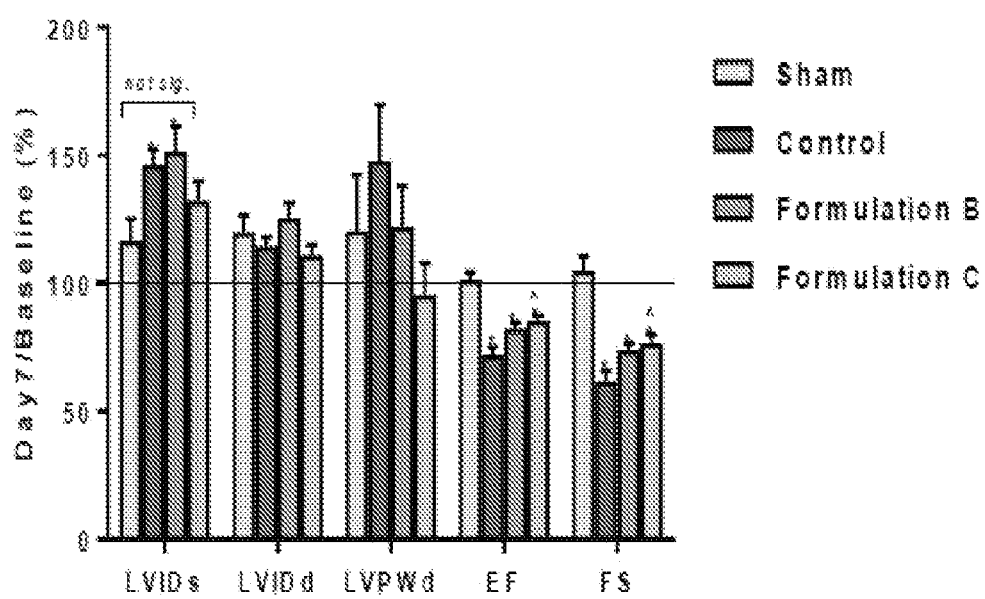
Figure 6:
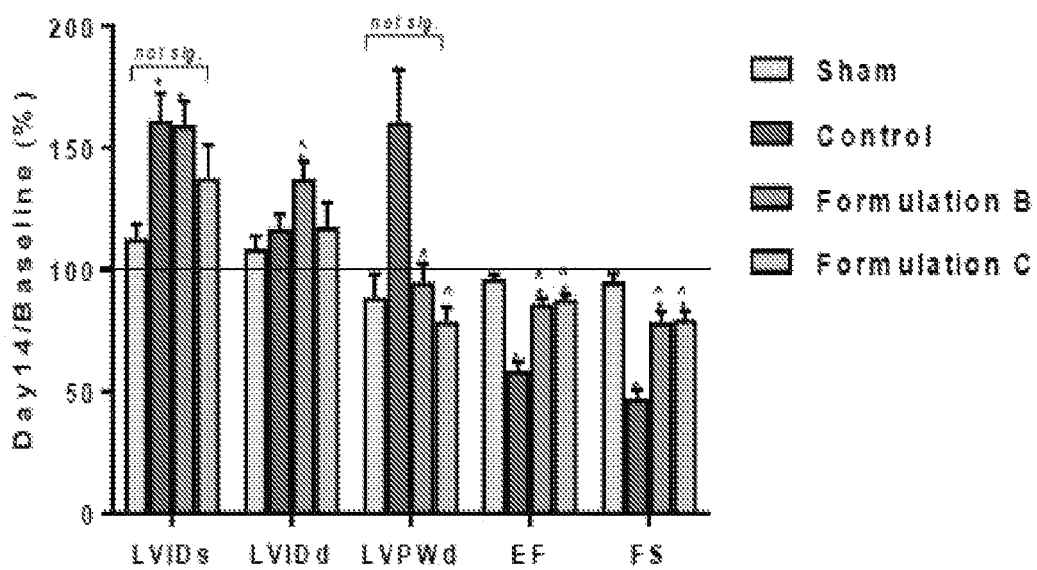

LVIDs, LVIDd, and LVPWd increased in all groups at 1 D after operation, and the EF and FS values decreased in all groups at 1 D after operation (see FIG. 6A). It is presumed that the injury is mainly caused by aortic constriction. In addition, the smallest changes were observed between the Sham group and Formulation C group, which suggests that Formulation C (apelin liposome) is more efficacious than Formulation B (apelin only) in treating the injury. FIG. 6B shows that, after 7 D, LVIDs, LVIDd, LVPWd increased in each group, with Sham group having the lowest increase. This suggests that surgical trauma was gradually restored in the administration groups, with Formulation C group increasing less. This result also suggests apelin continues to play a role at D 7. Sham group EF and FS were flat with Baseline, suggesting that the decreased cardiac function caused by the surgical trauma had been restored. Finally, as seen in FIG. 6C, at 14 D, the Sham group LVIDs, LVIDd, LVPWd, EF, and FS were flat with Baseline, suggesting that cardiac dysfunction caused by the surgical trauma had been restored. The changes were the greatest in the Control group as expected. In the two treatment groups, all the indexes showed that the drug was effective and the change of Formulation C group was the closest to Sham group. This result suggests that the apelin liposome is superior to apelin alone in treating the injury.

Figure 7:
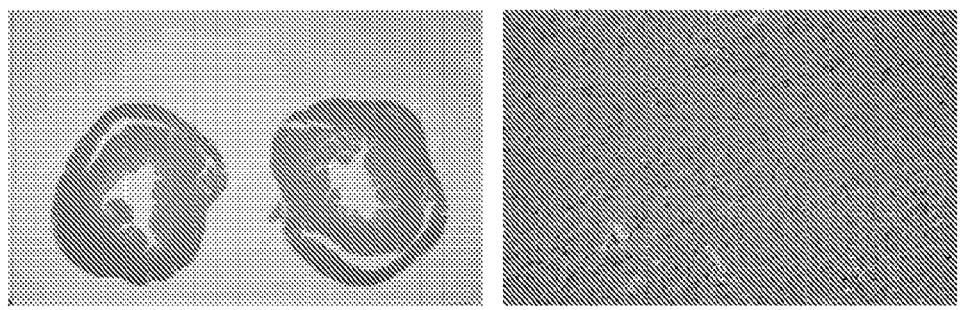
FIGS. 7A-7D show representative H&E staining images showing cardiac structural integrity.
Figure 7:
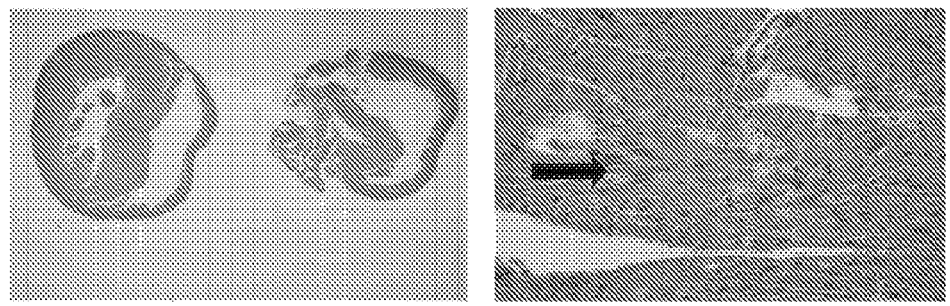
Figure 7:
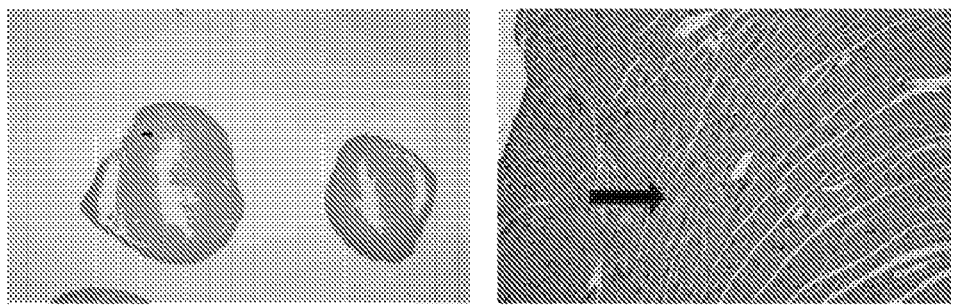
Figure 7:
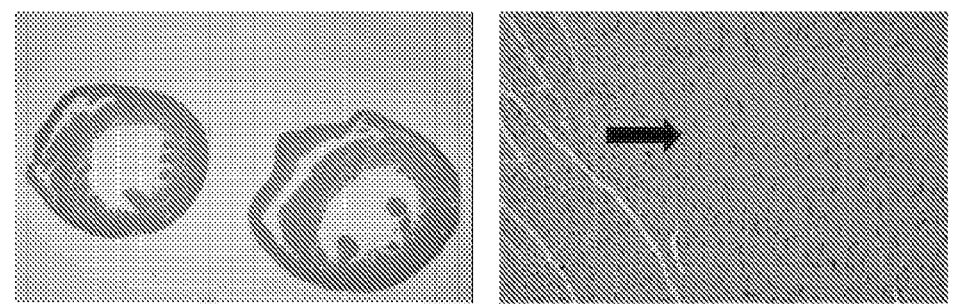
Figure 8:
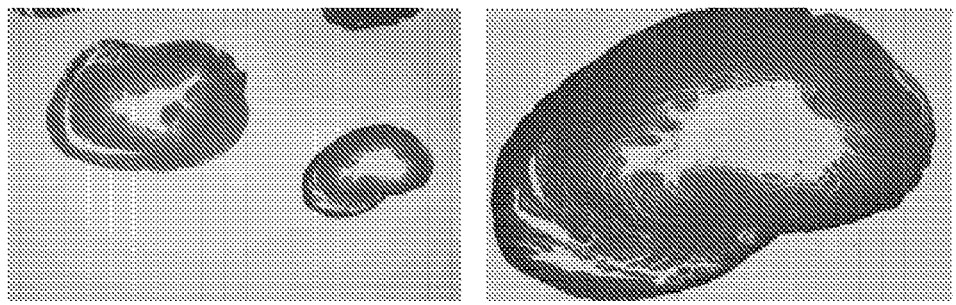
FIGS. 8A-8D show representative MASSON staining images showing cardiac structural integrity.
Figure 8:
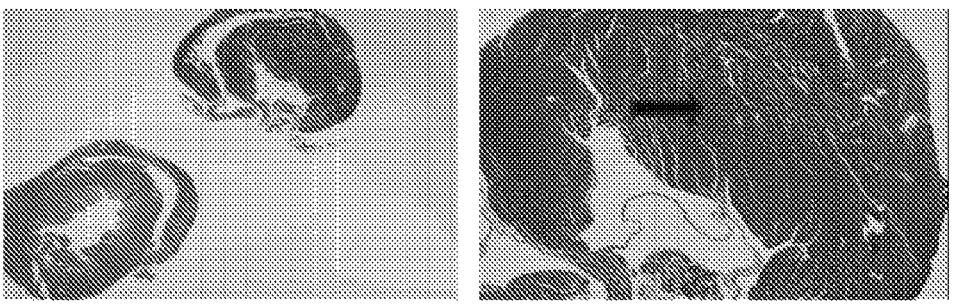
Figure 8:
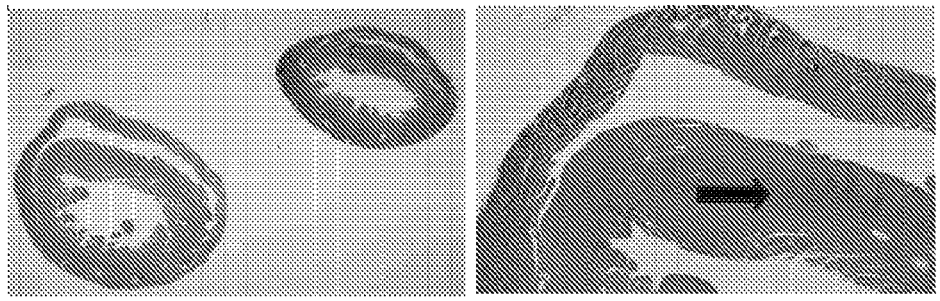
Figure 8:
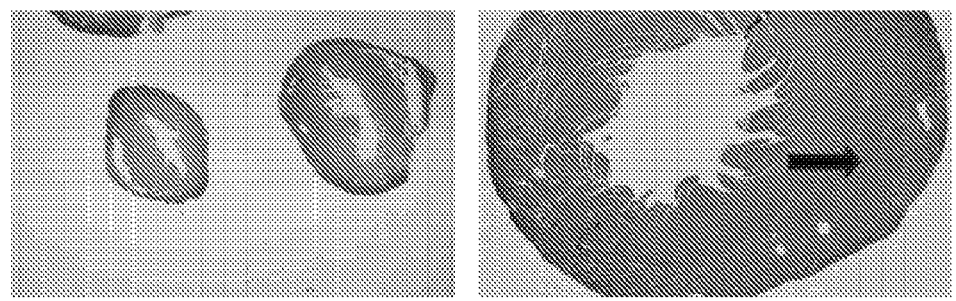

At the end of the experiment, all the mice were sacrificed and histological analysis was conducted. With HE staining, as shown in FIGS. 7A-7D, the Sham group had orderly and evenly distributed myocardium and thin vascular walls (FIG. 7A). In contrast, the Control group had damaged cardiac structural integrity, myocardial arrhythmias, swelling and thickening of the vascular wall (FIG. 7B). Mice treated with Formulation B showed cardiac structures with maintained integrity, orderly arrangement of myocardium, but also large myocardial interstitial that showed multiple myocardial infarction or bleeding (FIG. 7C). Mice treated with Formulation C also showed cardiac structures with maintained integrity, orderly arrangement of myocardium, exhibiting multiple myocardial infarctions or bleeding (FIG. 7D). The amount of myocardial infarctions or bleeding was less with Formulation C group (apelin liposome) compared with Formulation B (apelin alone). With Masson trichrome staining, as shown in FIGS. 8A-8D, the sham group had myocardium arranged in regular order-cardiac muscle cells with full, compact, thin vascular wall (FIG. 8A). There was a small amount of collagen deposition. In contrast, the Control group had a large area of collagen deposition (FIG. 8B). Mice treated with Formulation B showed significant myocardial collagen deposition (FIG. 8C), but not as much as observed in the Control Group. Mice treated with Formulation C showed only a small amount of collagen deposition (FIG. 8D) compared with Formulation B. The apelin liposome diminished fibrosis to a greater extent than apelin alone.

Both administrations, Formulation B (apelin alone) and Formulation C (apelin liposome) restored contractility (EF and FS) after induced heart failure. In addition, they inhibited hypertrophic growth as evidenced by attenuation of increases in LVIDs, LVIDd, and LVPWd after aortic constriction. In direct comparison, Formulation C (apelin liposome) provided more favorable therapeutic benefits compared with Formulation B (apelin alone).

Together, these data suggest that apelin liposomes can be used to treat cardiac hypertrophy and heart failure.

Example 2: Apelin Formulations in Treatment of Myocardial Infarction

Animal Experiment Protocol.

Male Sprague-Dawley rats (age, 8-years-old) weighing 180-220 g are obtained from standard source. Mice are maintained in a temperature-controlled (20-22° C.) environment under a 12 h light-dark cycle. Rats are divided into three groups (n=6/group), as follows: Sham; left anterior descending artery (LAD) ligation; and LAD+apelin groups. Apelin groups receive apelin liposomes according to the formulations set forth in Table 4 below.

TABLE 4

| Treatment formulations | | |
|---|---|---|
| | APL #1 Weight % | APL #2 Weight % |
| DSPC | 25.00% | 10.00% |
| DPPC | 25.00% | 10.00% |

TABLE 4-continued

| Treatment formulations | | |
|---|---|---|
| | APL #1 Weight % | APL #2 Weight % |
| Poloxamer 188 | 8.33% | 15.00% |
| PEG 8000 | 16.67% | 15.00% |
| [Pyr1]-Apelin-13 | 25.00% | 45.00% |
| Cholesterol | — | 5.00% |
| TOTAL | 100.00% | 100.00% |

Rats in the LAD group undergo an LAD ligation operation (Patten 1998; Ahn 2004). Briefly, rats are anesthetized with 10% chloral hydrate (3.5 ml/kg) via intraperitoneal injection. In a supine position, endotracheal intubation is performed and the rats are ventilated using a rodent ventilator (rate, 80 breaths/min; tidal volume, 6-8 ml/kg). The thoracic cavity is then opened and the heart was exposed. The LAD is ligated using 7-0 silk. Successful LAD ligation is confirmed by myocardial blanching and the thoracic cavity is closed layer-by-layer. Following LAD ligation operation, rats receive an intramuscular injection of $2.5 \times 10^4$ U penicillin. Rats in the sham group receive an equivalent operation, but without ligation. Rats in the LAD+apelin group receive an intraperitoneal injection with apelin dosing every day for 4 weeks following the LAD ligation operation. Rats in the sham and LAD groups receive an equal amount of normal saline. After 4 weeks, rats in each group are anesthetized with 10% chloral hydrate. The levels of left ventricular systolic pressure (LVSP), left ventricular end-diastolic pressure (LVEDP), left ventricular maximal rate of pressure rise (LV+dp/dtmax) and left ventricular maximal rate of pressure decline (LV−dp/dtmax) are measured. The rats are anesthetized with 10% chloral hydrate (3.5 ml/kg; intraperitoneal injection). The blood is harvested and stored at room temperature for 2-4 h and centrifuged at 4,000 rpm for 10 min. The supernatant is collected and the serum is obtained. All animal experiments are performed according to the Guide for the Care and Use of Laboratory Animals.

It is contemplated that treatment with the apelin liposomes will result in one or more of the follow outcomes: relieves myocardial infarction-induced left ventricular dysfunction (e.g., LVSP, LVEDP); attenuates myocardial infarction-induced myocardial fibrosis (measured by Masson's trichrome staining); decrease fibrosis markers (e.g., TGF-β, CTGF, Col-I, MMP-2 and MMP-9); and reduces Angiotensin II and NF-κB levels.

Example 3: Apelin Formulations in Treatment of Pulmonary Hypertension (PAH)

Twenty patients with PAH will participate in a randomized double-blind placebo-controlled study of apelin liposomes and matched saline placebo infusions during right heart catheterization (Vestbo 2013; Vestbo 2015). Apelin groups receive apelin liposomes according to the same formulations set forth above at Table 4.

Mean pulmonary artery pressure, pulmonary artery wedge pressure and cardiac output are measured. It is contemplated that treatment with the apelin liposomes will result in increase in cardiac output.

Example 4: Apelin Formulations in Treatment of Diabetes

Healthy overweight men are enrolled in a randomized, double-blind, placebo-controlled, cross-over study that successively considered the efficacy and the tolerance of two doses of apelin liposomes. A first group of subjects will receive dosing of apelin liposomes and, after examination of safety data, a second group will receive a higher dose (n=8). Apelin groups receive apelin liposomes according to the formulation set forth in Table 4 above.

Each volunteer is subjected to two hyperinsulinemic-euglycemic clamps where the basal level of glucose infusion rate (GIR) is measured from the 90th to the 120th minutes (level 1). Apelin or placebo continuous i.v. administration is then started for 2 hours and GIR is finally evaluated from the 210th to the 240th minutes (level 2). Primary evaluation endpoint is the difference in GIR between level 2 and level 1 (ΔGIR). It is contemplated that treatment with the apelin liposomes will result in an increase in ΔGIR vs. control.

Example 5: Apelin Formulations in Treatment of Diabetic Nephropathy

Breeding pairs of Akita (Insulin2+/−) mice on a C57BL/6 background are obtained.

Animals are housed in ventilated microisolator cages with free access to water and food in a temperature-controlled room (22±2° C.) with a 12 h light-dark cycle. Male Akita mice (Insulin2+/−) and their non-diabetic littermates (Insulin2+/+, wild type (WT)) are used in the present study.

Mice are separated into four groups: PBS-treated WT mice (WT); apelin-treated WT mice (WT+Ap); PBS-treated Akita mice (AK); and apelin-treated Akita mice (AK+Ap). The experiments start at 9 weeks of age, since male Akita mice begin to show hyperglycemia at 4-7 weeks of age. Therefore, the symptoms of animals at the start of experiments are similar to those of early-stage diabetic patients. Apelin liposomes are administrated to Akita mice via tail vein injection twice per day. Apelin groups receive apelin liposomes according to the formulations set forth in Table 4 above.

In the present study, apelin liposomes or PBS is injected via the tail vein from the most distal end to the root of the tail. Animals will undergo terminal anesthesia at 19 weeks with chloral hydrate (IP, 500 mg kg-1) to enable harvesting of kidneys and serum, which result in subsequent death by exsanguinations.

It is contemplated that treatment with the apelin liposomes will result in one or more of the follow outcomes: inhibits diabetes-induced renal dysfunction (e.g., kidney weight, kidney index (KI), proteinuria, albumin/globulin (A/G), and glomerular filtration rate (GFR)) and renal histological changes; inhibits diabetes-induced histone hyperacetylation (e.g., ac-H3K9, ac-H3K18, and ac-H3K23) in the kidney by upregulating HDAC; inhibits diabetes-induced renal inflammation (e.g., MCP-1, ICAM-1 and iNOS) in Akita mice. It is further contemplated that treatment with the apelin liposomes will result in one or more of the follow outcomes: inhibits renal hypertrophy; inhibits glomerular hypertrophy; reduces albuminuria; reduces monocyte infiltration; reduces renal inflammation (e.g., MCP1 and VCAM1 quantities decreased); and restores anti-oxidant catalase levels.

Example 6: Apelin Formulations in Treatment of Chronic Kidney Disease

Seven-week-old male C57Bl/6j mice (weighing approximately 20-22 g) are obtained. Animals are randomly assigned to four groups (n=5): (1) sham+vehicle, (2) UUO (unilateral ureteral obstruction)+vehicle, (3) UUO+apelin liposomes, and (4) sham+apelin liposomes. UUO is carried out using an established protocol (Jones 2009).

Briefly, the mice are anaesthetized with sodium pentobarbital (50 mg/kg body weight) and the left ureter was double ligated. Sham-operated mice will have their ureters exposed, but not ligated. Starting the day of surgery, the mice receive apelin liposomes or the vehicle alone by intraperitoneal injection every 24 h. Apelin groups receive apelin liposomes according to the formulations set forth in Table 4 above.

After 2 weeks, the mice are killed and their kidney tissues are removed for various analyses. It is contemplated that treatment with the apelin liposomes will result in one or more of the follow outcomes: ameliorates renal interstitial fibrosis (decreases fibrotic area by Masson's trichrome, decreases Fibronectin and Collagen I deposition); inhibits the expression of Epithelial-mesenchymal transition (EMT) markers (maintains laminin, preserves epithelial E-cadherin, and inhibits α-SMA (smooth muscle actin) expression); inhibits TGF-β1 and SMAD2 pathway (decreases TGF-β and TGF-β receptor levels and p-SMAD2 levels).

Example 7: Apelin Formulations in Treatment of Acute Kidney Disease

Animals and renal ischemia/reperfusion (I/R) model Male Wistar rats are obtained and housed in ventilated microisolator cages with free access to water and food. Rats weighing 180±20 g are used and assigned to one of the following groups: CT group, uninjured rats with vehicle administration; I/R group, rats underwent I/R injury with vehicle administration; I/R+Ap group, rats underwent I/R injury with apelin liposomes. Apelin groups receive apelin liposomes according to the formulations set forth at Table 4 above.

I/R injury is performed as described previously (Supavekin 2003). Briefly, rats are anesthetized and undergo midline abdominal incisions with their left renal pedicle bluntly clamped by a clamp for 30 min (unilateral renal occlusion). After removing the clamps, wounds are sutured and the animals allowed to recover for 3 days before sacrifice. Control animals were sham operated.

It is contemplated that treatment with the apelin liposomes will result in one or more of the follow outcomes: protects against renal I/R injury induced morphological and functional changes (morphological change from HE staining; renal dysfunction includes increased urine volume, proteinurea, and creatinine discharge); suppresses I/R injury induced inflammation and apoptosis in kidneys (decreases inflammation markers MCP-1 and ICAM-1, decreases apoptosis markers caspase-3 and caspase-8); inhibits histone hypermethylation in kidneys (decreases H3K4me2 and H3K79me1); and inhibits I/R induced up-regulation of Tgf-β1 (decreases Tgf-β1 levels).

Example 8: Apelin Formulations in Treatment of Erectile Dysfunction (ED)

Male C57BL/6J mice will be used in this study. Two different vasculogenic ED models can be used to examine the differential gene expression of apelin and APJ in the corpus cavernosum tissue. One model is an acute cavernous ischemia model induced by bilateral occlusion of the internal iliac arteries. The other model is a chronic vasculogenic ED model in which either hypercholesterolemia or diabetes was induced by feeding a high-cholesterol diet or by intraperitoneal injection of STZ, respectively.

For the acute cavernous ischemia model, 12-week-old C57BL/6J mice are anesthetized with ketamine (100 mg/kg) and xylazine (5 mg/kg) intramuscularly and placed supine on a thermoregulated surgical table. After a low midline abdominal incision was made, the internal iliac artery is clamped and ligated bilaterally just distal to the bifurcation of the common iliac artery.

For the chronic vasculogenic ED model, 8-week old C57BL/6J mice are either fed a diet containing 4% cholesterol and 1% cholic acid for 3 months or receive intraperitoneal injections of multiple low doses of STZ (50 mg/kg body weight in 0.1 M citrate buffer, pH 4.5) for 5 days consecutively as described previously (see, e.g., Jin 2009; Ryu 2009).

The serum total cholesterol level is determined with commercially available kits (e.g., Boehringer Mannheim GmBH, Mannheim, Germany) and an automatic analyzer (e.g., HITACHI 7600, Hitachi Koki Co., Hitachinaka, Japan) 3 months after initiation of the high-cholesterol diet. Fasting and postprandial blood glucose levels are measured with a standard blood glucose meter (e.g., Accu-check, Roche Diagnostics, Mannheim, Germany) before and 2 months after intraperitoneal injection of STZ. The messenger RNA (mRNA) levels of apelin and APJ is determined in the corpus cavernosum tissue of each vasculogenic ED model (0, 1, 3, 6, 12, 24, and 72 hours after bilateral occlusion of the internal iliac artery; 3 months after initiation of the high-cholesterol diet; and 2 months after intraperitoneal injection of STZ) and in age-matched controls by the use of semiquantitative RT-PCR.

The effectiveness of apelin protein in restoring erectile function in a mouse model of hypercholesterolemic ED will also be determined. Three months after initiation of the high-cholesterol diet, the optimal dose of apelin for the recovery of erectile function 1 day after a single intracavernous injection of apelin liposomes will be determined based on the dose having the highest erectile function recovery in hypercholesterolemic mice treated with apelin.

On the basis of this initial study, the animals will be divided into three groups: group 1, age-matched controls; group 2, hypercholesterolemic mice that receive a single intracavernous injection of PBS (20 mL); and group 3, hypercholesterolemic mice that receive a single intracavernous injection of apelin liposomes. Apelin groups receive apelin liposomes according to the formulations set forth at Table 4 above.

Erectile function by electrical stimulation of the cavernous nerve (N=6 per group) 1 day after treatment and the penis will be determined and then specimens will be harvested for histologic examination. Cavernous specimens from a separate group of animals will be used for Western blot analysis (N=4 per group).

It is contemplated that treatment with the apelin liposomes will result in one or more of the follow outcomes: erectile response to cavernous nerve stimulation increases significantly in hypercholesterolemic mice that received apelin liposomes compared with that in hypercholesterolemic mice that received PBS (or other control); increases cavernous eNOS phosphorylation and decreases cavernous endothelial cell apoptosis by reducing the generation of reactive oxygen species (ROS), such as superoxide anion.

Example 9: Apelin Formulations

Apelin liposomes were formed using the following protocol. Liposome components are outlined in Table 5 below.

TABLE 5

Liposome components

| Component | Weight % | Weight (mg) |
|---|---|---|
| Poloxamer188 | 98% | 150 mg |
| DSPC (Mw: 387) | 29.4% | 450 mg |
| DPPC (Mw: 734.04) | 29.4% | 450 mg |
| PEG 8000 | 19.6% | 300 mg |
| Apelin | 11.8% | 180 mg |
| TOTAL | 100.0% | 1530 mg |

Briefly, DSPC (450 mg) and DPPC (450 mg) were dissolved in ethanol (minimum amount), sonication until completely dissolved. PEG 8000 (300 mg) and Poloxamer 188 (150 mg) were taken in methanol, sonication until completely dissolved. The two solutions were mixed in one vial. Then nitrogen was bubbled to remove the solvent. The final solid was dried in vacuum for 3 hrs. The lipid film was dissolved in citric acid (300 mmol) solution. The film was suspended for 15 min and filtered with a polycarbonate 0.2 nm size. The mixture was exchanged with distilled water by dialysis and then lyophilization. Apelin (180 mg) was then dissolved in distilled water and added to the lipid film, additional water was added during slowly mixing for about 30 min to 1 h. And then the liposome was incubated at 37° C. for 90 min. and then lyophilization.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

REFERENCES

1. Ahn et al. Am J Physiol Heart Circ Physiol 286(3):H1201-1207 (2004)
2. Chakrabarti et al. Food Sci Human Wellness 5(1):1-7 (2016)
3. Erdmann et al. J Nutr Biochem 19(10):643-654 (2008)
4. Jin et al J Sex Med 6(12):3289-3304 (2009)
5. Jones et al Nephrol Dial Transplant 24(10):3024-3032 (2009)

6. Patten et al. Am J Physiol 274(5 Pt 2):H1812-H1820 (1998)
7. Ryu et al J Sex Med 6(7):1893-1907 (2009)
8. Supavekin et al. Kidney Int 63(5):1714-1724 (2003
9. Vestbo et al. Eur Respir J 41(5):1017-1022 (2013)
10. Vestbo et al., "Study to understand mortality and morbidity in COPD (SUMMIT)," Eur Respir J 46: Suppl. 59 (2015)

What is claimed is:

1. A composition comprising an apelin peptide that is at least partially encapsulated in a liposome comprising an amount of a poloxamer, 1,2-distearoyl-sn-glycero-3-phosphocholine (DSPC), 1,2-Dipalmitoyl-sn-glycero-3-phosphocholine (DPPC), and a polyethylene glycol (PEG),
   wherein the composition comprises between about 20 wt % and about 50 wt % of the apelin peptide,
   wherein the amount of the poloxamer is between about 1 wt % and about 20 wt %,
   wherein the amount of DSPC is between about 5 wt % and about 30 wt %,
   wherein the amount of DPPC is between about 5 wt % and about 30 wt %, and
   wherein the amount of the PEG is between about 10 wt % and about 20 wt %.

2. The composition of claim 1, wherein the apelin peptide is selected from the group consisting of apelin-12, apelin-13, pyroglutamyl apelin-13 ([Pyr1]-apelin-13), apelin-17, apelin-19, and apelin-36.

3. The composition of claim 1, wherein the poloxamer is poloxamer 124, poloxamer 181, poloxamer 184, poloxamer 188, poloxamer 331, and poloxamer 407, or any combination thereof.

4. The composition of claim 1, wherein the PEG has an average molecular weight of from about 200 to about 20000 daltons (PEG 200 to PEG 20000).

5. The composition of claim 4, wherein the PEG has an average molecular weight of about 8000 daltons (PEG 8000).

6. The composition of claim 2, wherein the composition comprises between about 20 wt % and about 30 wt % of the apelin peptide.

7. The composition of claim 1, wherein the amount of the poloxamer is between about 2 wt % and about 12 wt %.

8. The composition of claim 1, wherein the amount of DSPC is between about 20 wt % and about 30 wt %.

9. The composition of claim 1, wherein the amount of DPPC is between about 20 wt % and about 30 wt %.

10. The composition of claim 1, wherein the amount of the PEG is between about 12 wt % and about 18 wt %.

11. The composition of claim 1, further comprising an amount of cholesterol.

12. The composition of claim 11, wherein the amount of cholesterol is between about 1 wt % and about 10 wt %.

13. The composition of claim 1, further comprising a pharmaceutically acceptable excipient.

14. The composition of claim 1, further comprising at least one additional therapeutic agent.

15. The composition of claim 1, wherein the composition comprises about 25 wt % of the apelin peptide, about 8 wt % poloxamer 188, about 25 wt % DSPC, about 25 wt % DPPC, and about 17 wt % PEG 8000.

16. The composition of claim 11, wherein the composition comprises about 45 wt % of the apelin peptide, about 15 wt % poloxamer 188, about 10 wt % DSPC, about 10 wt % DPPC, about 15 wt % PEG 8000, and about 5 wt % cholesterol.

17. A method of treating or preventing a cardiovascular-related disease in a subject in need thereof, the method comprising administering a therapeutically effective amount of the composition of claim 1, wherein the cardiovascular-related disease is heart failure or myocardial infarction.

18. The method of claim 17, wherein the composition is administered intravenously, subcutaneously, orally, or via inhalation.

19. A method of preparing the composition of claim 1, comprising:
- dissolving the DSPC and the DPPC in ethanol and sonicating until dissolved to form a first composition;
- dissolving the PEG and the poloxamer in ethanol and sonicating until dissolved to form a second composition;
- forming a lipid film from the first composition and the second composition; and
- mixing the apelin peptide with the lipid film to form a liposome.

20. The composition of claim 12,
wherein the composition comprises between about 35 wt % and about 50 wt % of the apelin peptide,
wherein the amount of the poloxamer is between about 12 wt % and about 18 wt %,
wherein the amount of DSPC is between about 5 wt % and about 15 wt %,
wherein the amount of DPPC is between about 5 wt % and about 15 wt %,
wherein the amount of the PEG is between about 12 wt % and about 18 wt %, and
wherein the amount of cholesterol is between about 2 wt % and 8 wt %.

21. The composition of claim 1, wherein the apelin peptide is apelin-13.

22. The composition of claim 1, wherein the apelin peptide is pyroglutamyl apelin-13 ([Pyr1]-apelin-13).

* * * * *